(12) United States Patent
Shim et al.

(10) Patent No.: US 10,244,983 B2
(45) Date of Patent: Apr. 2, 2019

(54) MOBILE TERMINAL AND METHOD FOR CONTROLLING THE SAME

(71) Applicant: LG ELECTRONICS INC., Seoul (KR)

(72) Inventors: Hongjo Shim, Seoul (KR); Hyunok Lee, Seoul (KR); Youngho Sohn, Seoul (KR); Seonghyok Kim, Seoul (KR); Mihyun Park, Seoul (KR); Jisoo Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 505 days.

(21) Appl. No.: 14/973,304

(22) Filed: Dec. 17, 2015

(65) Prior Publication Data

US 2017/0020449 A1  Jan. 26, 2017

Related U.S. Application Data

(60) Provisional application No. 62/194,324, filed on Jul. 20, 2015.

(30) Foreign Application Priority Data

Sep. 10, 2015 (KR) ........................ 10-2015-0128611

(51) Int. Cl.
*A61B 5/00* (2006.01)
*A61B 5/053* (2006.01)
(Continued)

(52) U.S. Cl.
CPC ............ *A61B 5/4872* (2013.01); *A61B 5/002* (2013.01); *A61B 5/0022* (2013.01);
(Continued)

(58) Field of Classification Search
CPC ....... A61B 5/002; A61B 5/0022; A61B 5/053; A61B 5/0531; A61B 5/0537; A61B 5/4872

See application file for complete search history.

(56) References Cited

U.S. PATENT DOCUMENTS 7,031,750 B2 * 4/2006 Lee ..................... A61B 5/0002
455/556.1
7,031,767 B2 * 4/2006 Lin ...................... A61B 5/0537
379/207.02
(Continued)

FOREIGN PATENT DOCUMENTS

EP            2540221           1/2013

OTHER PUBLICATIONS

European Patent Office Application Serial No. 15202877.5, Search Report dated Dec. 16, 2016, 11 pages.

*Primary Examiner* — Max Hindenburg
(74) *Attorney, Agent, or Firm* — Lee Hong Degerman Kang & Waimey

(57) ABSTRACT

A mobile terminal includes: a terminal body forming an outer appearance; a wireless communication unit configured to perform wireless communication with an external device including a first electrode unit installed to be in contact with a part of a user's body; a second electrode unit disposed in a region of the terminal body and brought into contact with the user's body to form a closed sloop with the first electrode unit; and a control unit configured to form a body fat measurement result using a voltage formed by a current flowing between the first and second electrode units.

19 Claims, 35 Drawing Sheets

(51) Int. Cl.
*G06F 1/16* (2006.01)
*H04M 1/725* (2006.01)
*G06F 19/00* (2018.01)
*G16H 40/67* (2018.01)

(52) U.S. Cl.
CPC .......... *A61B 5/0077* (2013.01); *A61B 5/0537* (2013.01); *A61B 5/681* (2013.01); *A61B 5/6898* (2013.01); *A61B 5/742* (2013.01); *A61B 5/7405* (2013.01); *A61B 5/7455* (2013.01); *G06F 1/163* (2013.01); *G06F 19/00* (2013.01); *G16H 40/67* (2018.01); *H04M 1/7253* (2013.01); *H04M 2250/12* (2013.01)

(56) References Cited

U.S. PATENT DOCUMENTS

| | | | |
|---|---|---|---|
| 8,818,499 B2 * | 8/2014 | Karo | A61B 5/1072 |
| | | | 600/382 |
| 9,101,261 B2 * | 8/2015 | Kim | A61B 5/00 |
| 9,259,169 B2 * | 2/2016 | Hamaguchi | A61B 5/0537 |
| 9,314,186 B2 * | 4/2016 | Murakawa | A61B 5/4872 |
| 9,408,553 B2 * | 8/2016 | Hamaguchi | A61B 5/0537 |
| 9,723,997 B1 * | 8/2017 | Lamego | A61B 5/0205 |
| 9,742,902 B2 * | 8/2017 | Shimuta | H04M 1/72569 |
| 9,895,078 B2 * | 2/2018 | Eom | A61B 5/0537 |
| 2007/0100252 A1 | 5/2007 | Chou et al. | |
| 2011/0159469 A1 | 6/2011 | Hwang et al. | |
| 2015/0005653 A1 | 1/2015 | Michaelis et al. | |

* cited by examiner

MOBILE TERMINAL AND METHOD FOR CONTROLLING THE SAME

CROSS-REFERENCE TO RELATED APPLICATION

Pursuant to 35 U.S.C. § 119, this application claims the benefit of earlier filing date and right of priority to Korean Application No. 10-2015-0128611, filed on Sep. 10, 2015, and also claims the benefit of U.S. Provisional Application No. 62/194,324, filed on Jul. 20, 2015, the contents of which are all incorporated by reference herein in their entirety.

BACKGROUND OF THE INVENTION

1. Field of the Invention

The present disclosure relates to a mobile terminal capable of measuring biometric information.

2. Background of the Invention

Mobile terminals refer to devices including a battery and a display unit, outputting information on a display unit by using power supplied from the battery, and formed to be portable by users. Mobile terminals include a device for recording and reproducing video and a device displaying a graphic user interface (GUI), and also includes a notebook computer, a cellular phone, glasses, watches, and game machines capable of displaying screen information.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. Efforts are ongoing to support and increase the functionality of mobile terminals. Such efforts include software and hardware improvements, as well as changes and improvements in the structural components.

Recently, a function of collecting biometric information by a sensor, or the like, included in a mobile terminal has been researched. However, in order to collect biometric information, a users' intentional measurement stage is required, causing user inconvenience.

SUMMARY OF THE INVENTION

Therefore, an aspect of the detailed description is to provide a mobile terminal capable of collecting body fact measurement information while a mobile terminal is in use.

To achieve these and other advantages and in accordance with the purpose of this specification, as embodied and broadly described herein, a mobile terminal includes: a terminal body forming an outer appearance; a wireless communication unit configured to perform wireless communication with an external device including a first electrode unit installed to be in contact with a part of a user's body; a second electrode unit disposed in a region of the terminal body and brought into contact with the user's body to form a closed sloop with the first electrode unit; and a control unit configured to form a body fat measurement result using a voltage formed by a current flowing between the first and second electrode units.

In an example related to the present disclosure, the second electrode unit may be formed in a region adjacent to an audio output unit configured to output hearing data, in a region adjacent to an input key forming a control command, or on a side surface of the terminal body. Thus, when the user's body comes into contact with the second electrode unit while the user using the mobile terminal, the body fat measurement result may be formed.

In an example related to the present disclosure, when a preset specific function is executed, the control unit may measure a voltage between the first and second electrode units to form the body fat measurement result. Thus, the body fat measurement result may be provided when the user requires to measure a fat mass, or the body fat measurement result may be provided regularly.

According to embodiments of the present disclosure, since body fat information of a human body is measured through the first electrode unit continuously in contact with a part of the user's body and the second electrode unit in contact with other region as necessary (or while a specific function is being performed), the body fat measurement result may be provided before the user knows it. Thus, there is no need for the user to bring a part of his or her body into contact with the two electrodes on purpose to receive the body fat measurement result.

Further scope of applicability of the present application will become more apparent from the detailed description given hereinafter. However, it should be understood that the detailed description and specific examples, while indicating preferred embodiments of the invention, are given by way of illustration only, since various changes and modifications within the scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF THE INVENTION

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1A:
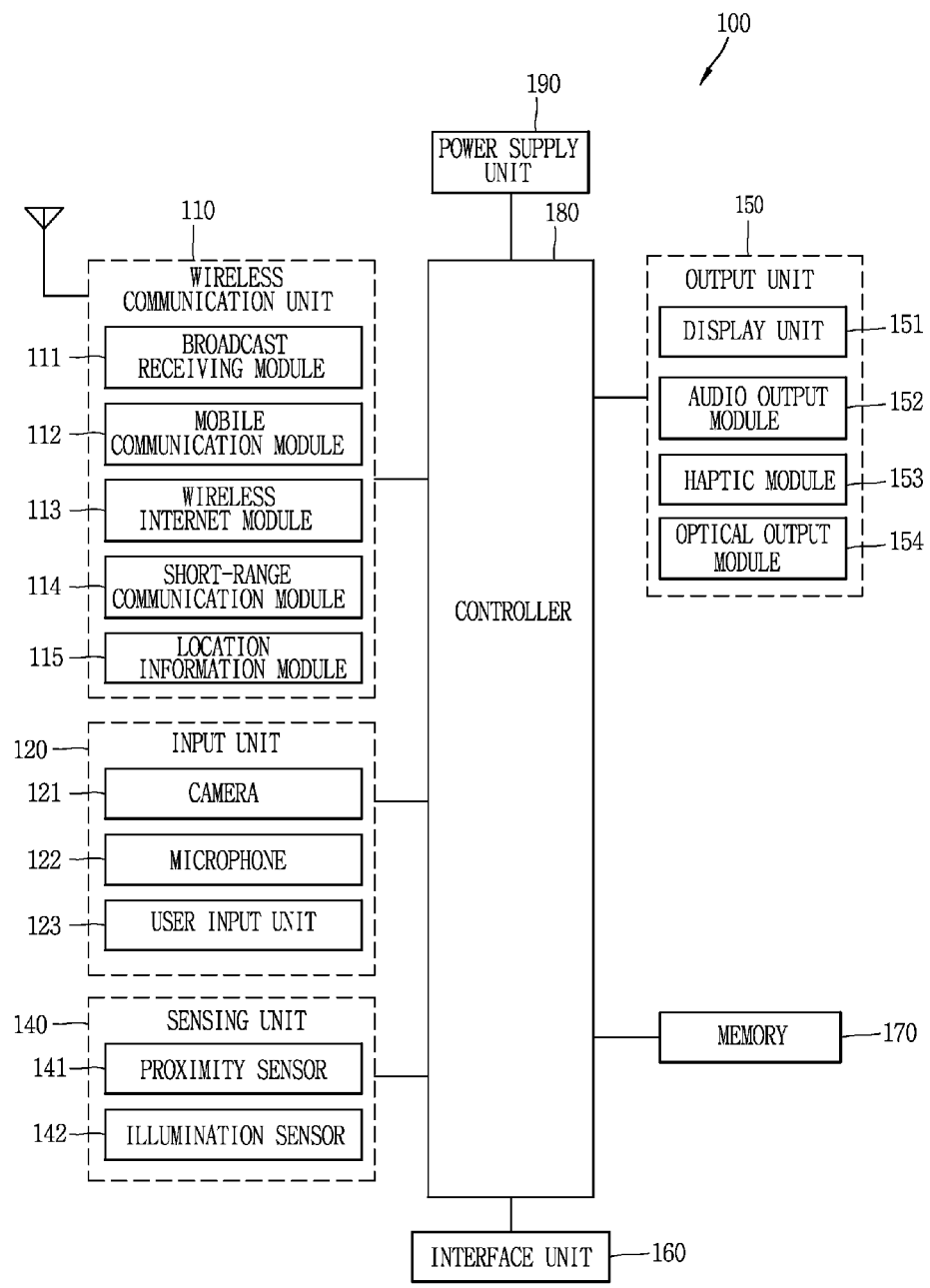
FIG. 1A is a block diagram of a mobile terminal in accordance with the present disclosure.
Figure 1B:
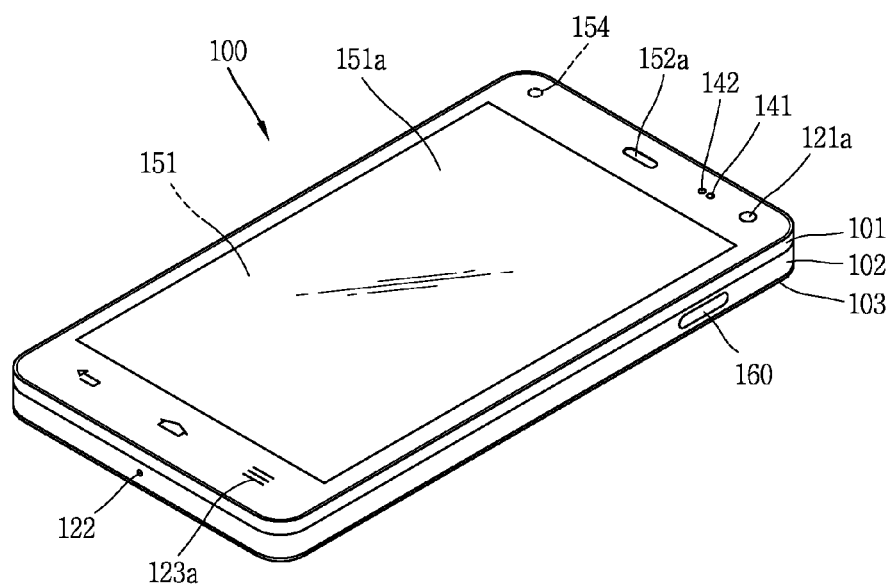
FIGS. 1B and 1C are conceptual views of one example of the mobile terminal, viewed from different directions.
Figure 1C:
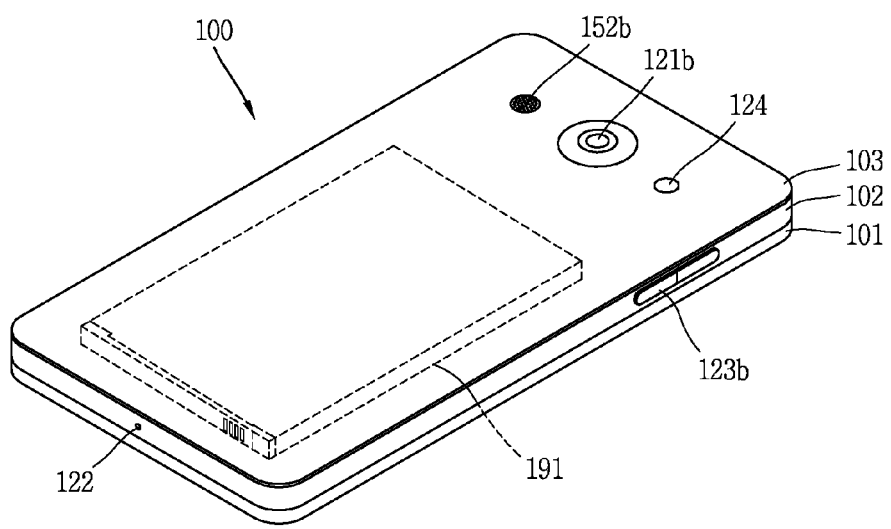

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions.

The mobile terminal 100 is shown having components such as a wireless communication unit 110, an input unit 120, a sensing unit 140, an output unit 150, an interface unit 160, a memory 170, a control unit 180, and a power supply unit 190. It is understood that implementing all of the illustrated components is not a requirement, and that greater or fewer components may alternatively be implemented.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server.

Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by control unit 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142. If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the control unit 180 to perform an operation (or function) for the mobile terminal 100.

The control unit 180 typically functions to control overall operation of the mobile terminal 100, in addition to the operations associated with the application programs. The control unit 180 may provide or process information or functions appropriate for a user by processing signals, data, information and the like, which are input or output by the various components depicted in FIG. 1A, or activating application programs stored in the memory 170. As one example, the control unit 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least some of the above components may operate in a cooperating manner, so as to implement an operation or a control method of a glass type terminal according to various embodiments to be explained later. The operation or the control method of the glass type terminal may be implemented on the glass type terminal by driving at least one application program stored in the memory 170.

Referring still to FIG. 1A, various components depicted in this figure will now be described in more detail.

Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like).

Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the control unit 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the control unit 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The control unit 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like). In general, control unit 180 processes data corresponding to proximity touches and proximity touch patterns sensed by the proximity sensor 141, and cause output of visual information on the touch screen. In addition, the control unit 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the control unit 180. Accordingly, the control unit 180 may sense which region of the display unit 151 has been touched. Here, the touch controller may be a component separate from the control unit 180, the control unit 180, and combinations thereof.

In some embodiments, the control unit 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The control unit 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images.

A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the control unit. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the control unit 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The control unit 180 may typically control the general operations of the mobile terminal 100. For example, the control unit 180 may set or release a lock state for restricting a user from inputting a control command with respect to applications when a status of the mobile terminal meets a preset condition.

The control unit 180 can also perform the controlling and processing associated with voice calls, data communications, video calls, and the like, or perform pattern recognition processing to recognize a handwriting input or a picture drawing input performed on the touch screen as characters or images, respectively. In addition, the control unit 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like.

As an alternative to the example in which the plurality of cases form an inner space for accommodating components, the mobile terminal 100 may be configured such that one case forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

FIGS. 1B and 1C depict certain components as arranged on the mobile terminal. However, it is to be understood that alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a.

The first audio output module 152a may be implemented in the form of a speaker to output voice audio, alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151a and the front case 101). In this case, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 154 to stop the light output.

The first camera 121a can process image frames such as still or moving images obtained by the image sensor in a capture mode or a video call mode. The processed image frames can then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 1B illustrates the first manipulation unit 123a as a touch key, but possible alternatives include a mechanical key, a push key, a touch key, and combinations thereof.

Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit (not shown) may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123a in the rear input unit. As such, in situations where the first manipulation unit 123a is omitted from the front side, the display unit 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

As shown in FIG. 1C, a flash 124 is shown adjacent to the second camera 121b. When an image of a subject is captured with the camera 121b, the flash 124 may illuminate the subject.

As shown in FIG. 1B, the second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

Figure 2A:
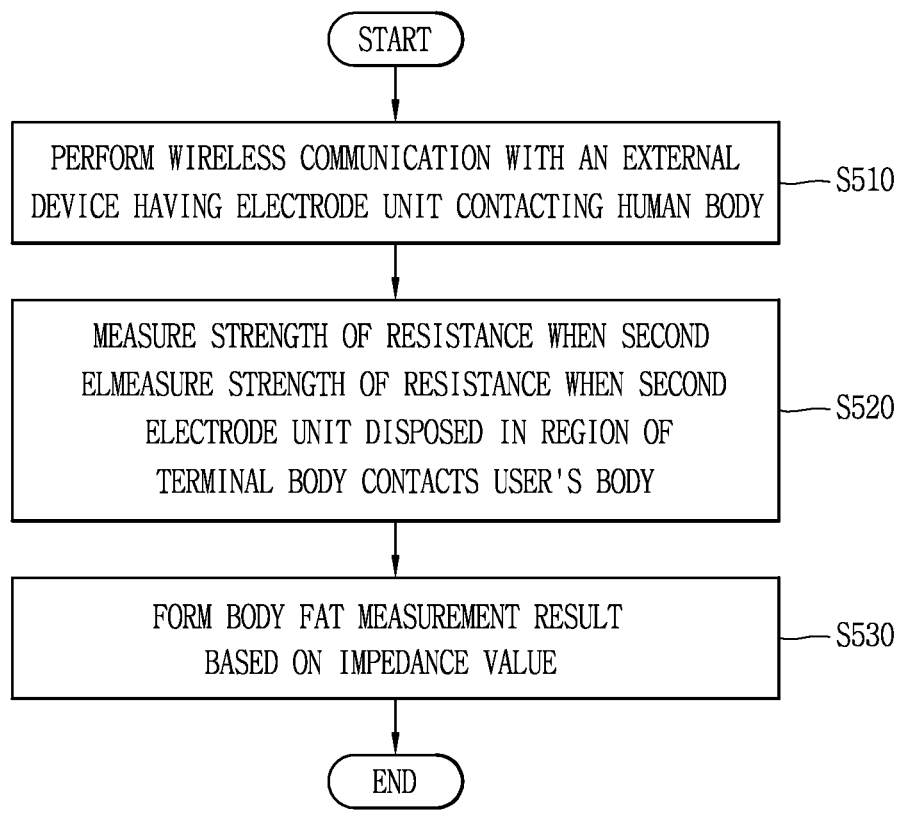
FIG. 2A is a flow chart illustrating a control method of a mobile terminal according to an embodiment of the present disclosure.
Figure 2B:
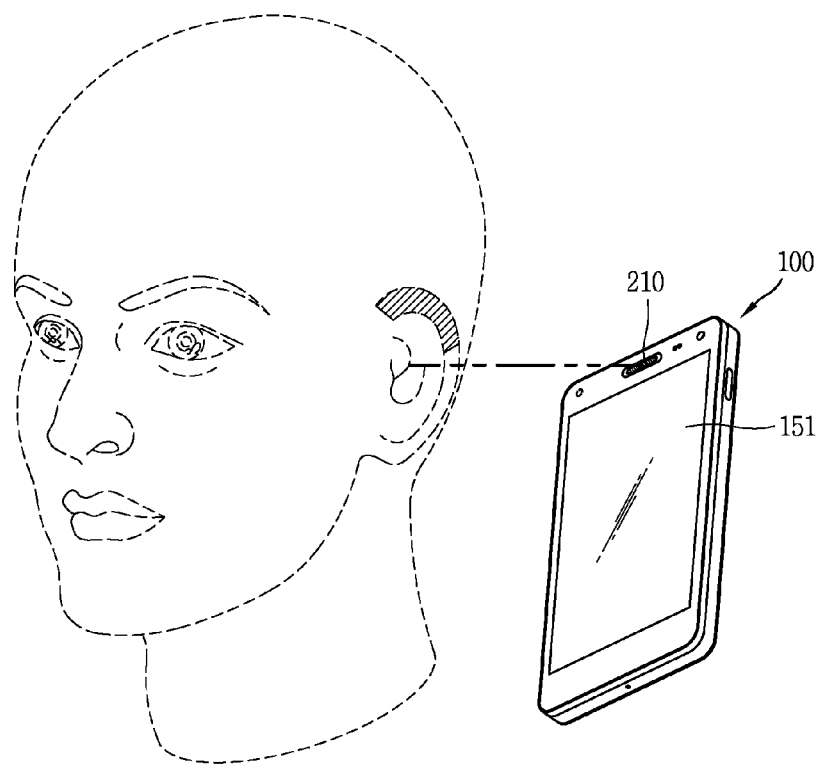
FIG. 2B is a conceptual view illustrating the control method of FIG. 2A.
Figure 2C:
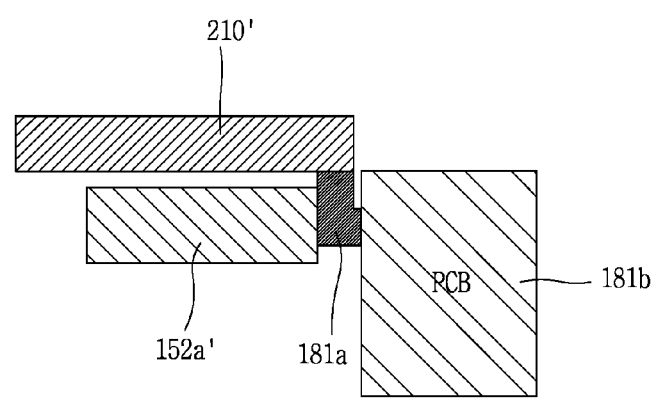
FIGS. 2C and 2D are conceptual views illustrating a structure of a second electrode unit.
Figure 2D:
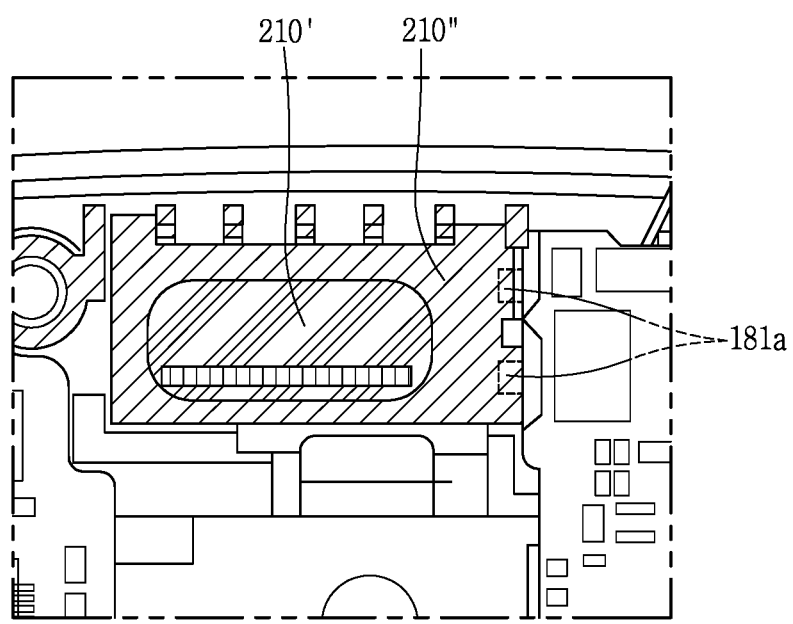
Figure 3A:
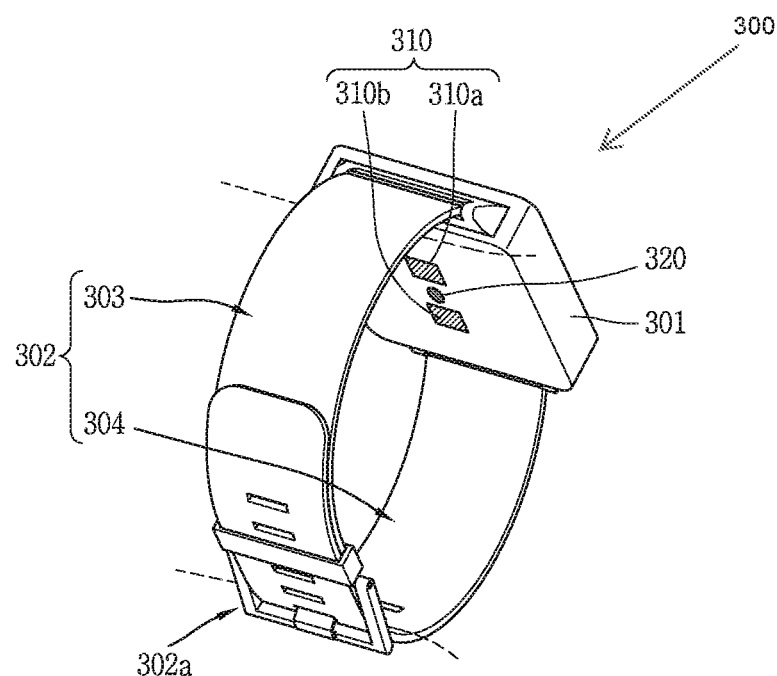
FIG. 3A is a conceptual view illustrating an external device including an electrode unit for measuring body impedance together with an electrode unit of a mobile terminal.
Figure 3B:
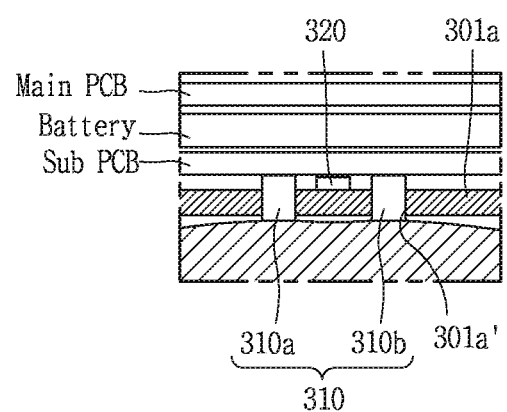
FIG. 3B is a conceptual view illustrating a structure of a first electrode unit.

FIG. 2A is a flow chart illustrating a control method of a mobile terminal according to an embodiment of the present disclosure. FIG. 2B is a conceptual view illustrating the control method of FIG. 2A. FIGS. 2C and 2D are conceptual views illustrating a structure of a second electrode unit. FIG. 3A is a conceptual view illustrating an external device including an electrode unit for measuring body impedance together with an electrode unit of a mobile terminal, and FIG. 3B is a conceptual view illustrating a structure of a first electrode unit.

Referring to FIGS. 2A through 3B, the mobile terminal performs wireless communication with an external device 300 including a first electrode unit 310 in contact with a part of a user's body. Referring to FIG. 3A, the external device 300 may be a watch type mobile terminal that can be worn on a user's wrist. The watch type mobile terminal 300 includes a main body 301 having a display unit (not shown) and a band 30s connected to the main body 301 and configured to be worn on a wrist. The main body 301 includes a case forming an outer appearance, and the case has an internal space accommodating various electronic components.

The watch type mobile terminal 300 is configured to perform wireless communication, and an antenna for wireless communication may be installed in the main body 301. Also, an audio output unit outputting a sound signal, a camera imaging an external environment, a microphone receiving a voice or a sound, and a user input unit may be provided within the main body 301.

The band 302 may be worn on a wrist to surround the wrist, and may be formed of a flexible material so as to be easily worn. For example, the band 302 may be formed of leather, rubber, silicon, or a synthetic resin material. Also, the band 302 may be detachably configured on the main body 301 so that the band 302 may be replaced with various types of bands. The band 302 may have a fastener 302a. The fastener 302a may be implemented into a buckle type, a snap-fit hook structure, a Velcro® type, or the like, and include a flexible section or material. The drawing illustrates an example that the fastener 302a is implemented using a buckle.

The first electrode unit 310 may be disposed in a region of the main body 301 and the band 302 such that the first electrode unit 310 is brought into contact with a user's skin when the watch type mobile terminal is worn on the user's wrist. It is illustrated that the first electrode unit 310 includes first and second electrode members 310a and 310b, but the number of the electrode members forming the first electrode unit 310 is not limited. Also, the external device 300 may further include a sensor 320 disposed to be adjacent to the first electrode unit 310 and collecting biometric information of the user. The sensor 320 may be configured as a photoplethysmography (PPG) sensor for measuring pulsation of the user, or the like. The first electrode unit 310 may be disposed on one surface of the main body 310 or on one surface of the band 302 which comes into contact with the user's body.

Referring to FIG. 3B, a cover 301a forming one surface of the main body 301 may include at least one opening hole 301a'. The number of opening holes 301a' corresponds to the number of electrode members forming the first electrode unit 310. The first and second electrode members 310a and 310b forming the first electrode unit 310 are in contact with user's skin through the opening holes 301a'. The first and second electrode members 310a and 310b may be formed to protrude, relative to a surface of the cover 301a.

Inside of the cover 301a, a sub-printed circuit board (PCB) electrically connected to the first and second electrode members 310a and 310b, a battery supplying electric power, and a main PCB may be sequentially stacked.

However, the external device is not limited thereto. The external device may be various types of wearable devices installed on a part of user's body or may be a device which includes an electrode unit and which can be continuously mounted on the user's body.

Referring to FIG. 2B, the second electrode unit 210 of the mobile terminal 100 is formed to be adjacent to the first audio output unit 152a. The second electrode unit 210 may be formed of a metal covering the first audio output unit 152a. For example, the second electrode unit 210 may be formed of SUS material. According to the present embodiment, when the user makes a call, the second electrode unit 210 may be brought into contact with the user's ear. Although not shown in detail, the second electrode unit 210 may protrude from an outer surface of the mobile terminal 100 by a preset height so as to be readily brought into contact with the user's body.

Referring to FIG. 2C, the second electrode unit 210 may function as a cover forming to cover a speaker module implementing the first audio output unit 152a. That is, the second electrode unit 210 covers the speaker module and is exposed outwardly. The speaker module and the second electrode unit 210 may be electrically connected to a printed circuit board (PCB) 181b through a contact terminal 181a. The second electrode unit 210 may be formed of a metal mesh such that a sound generated by the speaker module may be transmitted to the outside.

Referring to FIG. 2D, a metal extending portion 210" is in contact with a contact terminal 181a, and the outwardly exposed second electrode unit 210 may be disposed on the metal extending portion 210". Thus, while a sound output from the speaker module is emanated through the second electrode unit 210, a voltage may be measured through the second electrode unit 210 in contact with the user's body.

Figure 4:
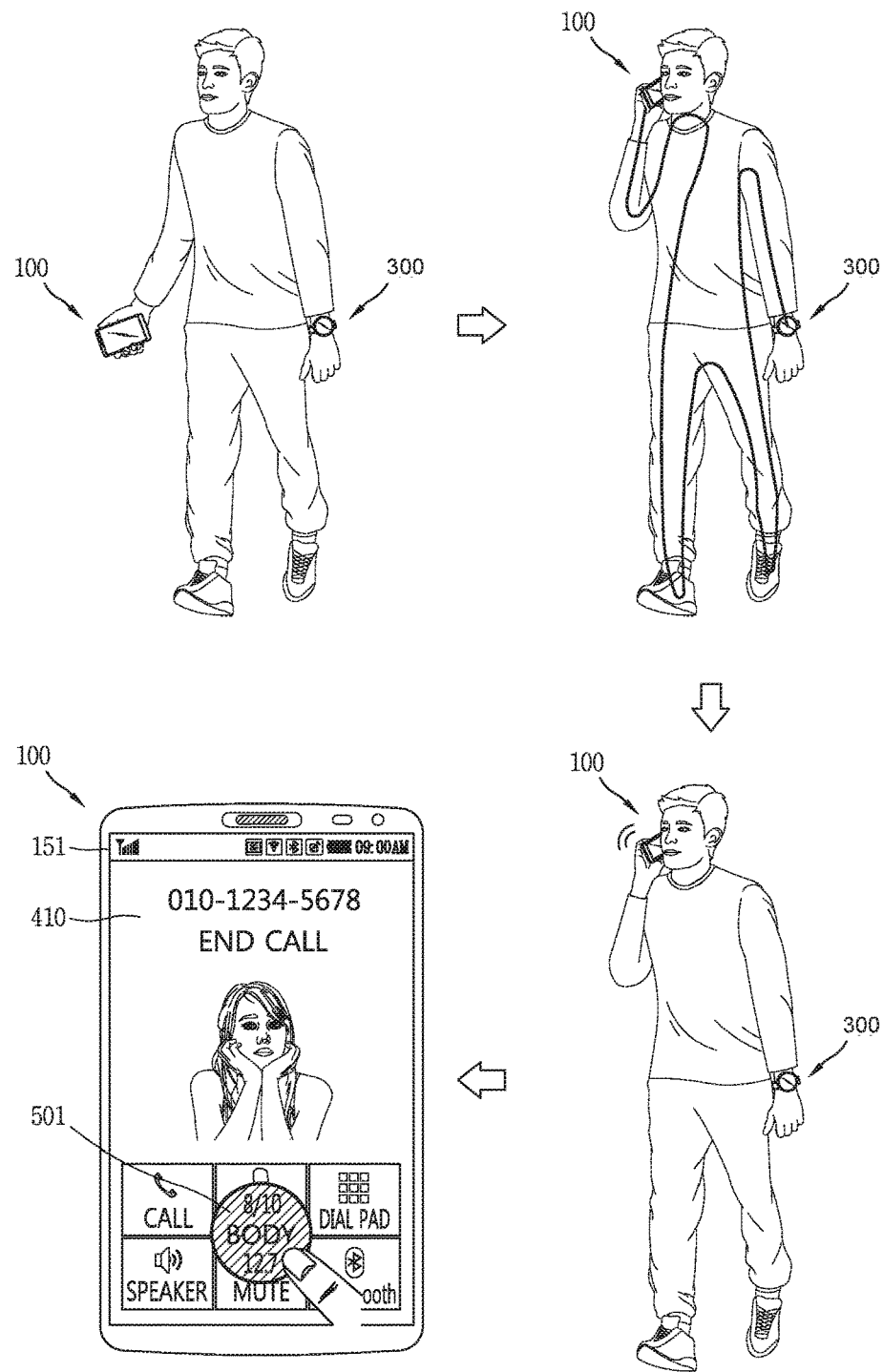
FIG. 4 is a conceptual views illustrating a mobile terminal including a second electrode unit according to various embodiments.

Referring to FIGS. 2A and 4, the first electrode unit 310 and the second electrode unit 210 supply a current and measure a current flowing in the body to measure impedance of the body. That is, the first electrode unit 310 may be formed as a transmission Tx electrode and the second electrode unit 210 may be formed as a reception Rx electrode. For example, the first electrode unit 310 applies a current having a preset strength. When the current transmitted through a part of the body is transmitted to the second electrode unit 210, a strength of a voltage may be measured (S520).

Meanwhile, the second electrode 210 may be formed to apply a current. For example, when a wireless signal indicating that the external device 300 has been worn on a body is received through the wireless communication unit, the control unit 180 may control the second electrode unit 210 to apply a current. Alternatively, the second electrode unit 210 may be controlled to apply a current while the mobile terminal is being operated or according to a preset period.

The control unit 180 obtains impedance information regarding a part of the body on the basis of the strength of the voltage between the first and second electrode units 310 and 210, and forms a body fat measurement result on the basis of the impedance information (S530).

Figure 5A:
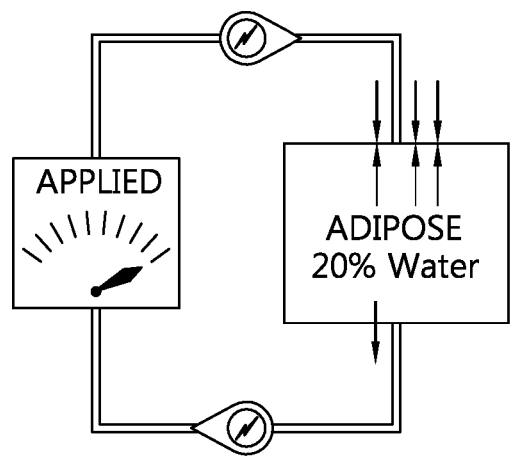
FIGS. 5A through 5C are conceptual views illustrating a principle for measuring body fat.
Figure 5B:
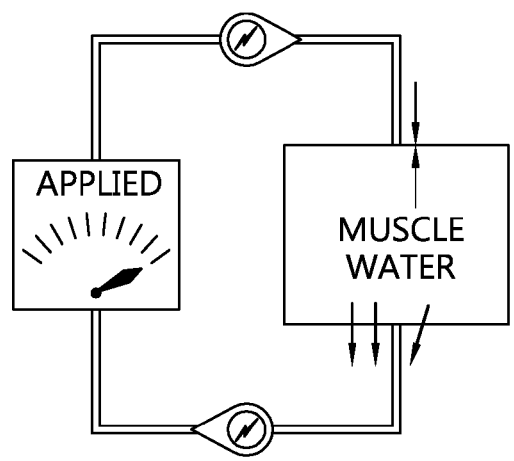
Figure 5C:
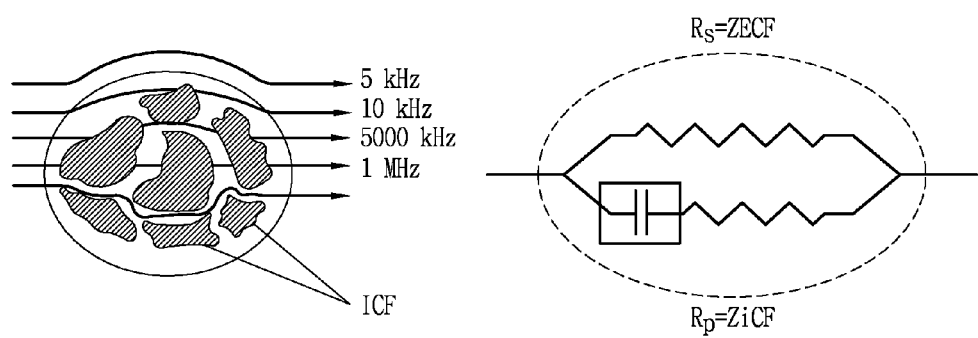

FIGS. 5A through 5C are conceptual views illustrating a principle for measuring body fat. Referring to FIGS. 5A and 5B together, electric conductivity of adipose and electric conductivity of muscle are different. Fat-free mass includes the largest amount of body water in the body and has conductive properties that it is easily conducted when a fine current is applied thereto, whereas body fat includes little moisture, having insulating properties in which a current cannot easily flow. A weight is determined by the sum of fat mass and a fat-free mass, and the fat-free mass is formed by the sum of a muscle mass and an inorganic mass.

Thus, even in a case in which the same current is applied, there is a difference in measured voltage values according to amounts of fat and muscle included in a part of the body in which the current flows. Adipose has insulating properties that a current cannot easily flow, and has a high impedance value. Muscle has properties such as a conductor in which a current flows readily flows, and has low impedance. That is, the control unit 180 may obtain a body fat measurement result of the body by using the impedance values.

Referring to FIG. 5C, elements of the body may be measured by adjusting a frequency. Among elements of cells of the body, membranes, which operate like resistive films, have characteristics that impedance is lowered when a frequency is increased. That is, a low frequency passes through only an outside of tissues of cells, while a high frequency forms a path within and outside of tissues of cells. For example, conductivity of an outer layer of skin may be measured by a current of about 1 KHz, and impedance of elements of the body may be measured by about 50 KHz. Thus, the first and second electrode units 310 and 210 may allow a current to reach cells by using a high frequency.

That is, considering that a body is regarded as a resistor, when a low current having a specific frequency (about 50 KHz) is applied between the first and second electrode units 310 and 210, a voltage is formed. Thus, by using a voltage and a current, impedance information regarding a part of the body in which a current has flown between the first and second electrode units 310 and 210 may be obtained. For example, the control unit 180 may obtain an impedance value regarding a part of the body between the external device 300 and the mobile terminal 200 and correct the impedance value on the basis of user information (age, gender, height, and weight) to form a body fat measurement result including a muscle mass and fat mass.

Referring to FIG. 4, the user wears the external device 300 such that the first electrode unit 310 comes into contact with the body. When brought into contact with the body, the control unit 180 obtains impedance information according to a voltage value between the first and second electrode units 310 and 210 on the basis of a current. Although not shown in detail, the mobile terminal 100 may further include a chip forming impedance information by a voltage.

The mobile terminal according to the present embodiment includes the second electrode unit 210 disposed to be adjacent to the first audio output unit 152a. For example, while a call function is being executed, the user's ear may be in contact with the second electrode unit.

When it is sensed that the second electrode unit 210 is in contact with a part of the user's body, the control unit 180 may obtain the impedance information. Here, in a case in which the current flows in the body for a preset period of time, the control unit 180 may calculate the impedance information, while in a case in which the first and second electrode units 310 and 210 come into contact with the body for a period of time less than the preset period of time, the control unit 180 does not form impedance information. A current output from the first electrode unit 310 flows from the user's left hand to the left leg, the right leg, and the body (trunk), and reaches the second electrode unit 210 in contact with the user's right ear, whereby a voltage between the first and second electrode units 310 and 210 may be calculated.

Also, although not shown, while the current flows, the control unit 180 may activate a specific sensor unit installed in the mobile terminal 100 or in the external device 300. The sensor unit may sense a movement of the user or a heart rate of the user.

In a case in which a user's movement sensed by the sensor unit is equal to or greater than a reference value or the heart rate is higher than a reference value, the control unit 180 may limit calculating the impedance information. Thus, the user may be provided with the impedance information measured in a state in which the body is stable.

In a case in which a current flows in the body by the first and second electrode units 310 and 210, the control unit 180 may output notification information. For example, the first audio output unit 152a may output a notification sound (a measurement start notification sound or a measurement termination notification sound) or the haptic module 153 may output vibrations.

Although not shown specifically, in a case in which the notification information is output and the body in contact with the second electrode unit 210 is released, the control unit 180 may stop measurement. Alternatively, when a specific type control command is applied to the user input unit 123, the control unit 180 may stop the measurement step.

For example, while a call function is being executed, the display unit 151 may output a first execution screen 410, and when the impedance information is obtained, the control unit 180 may control the display unit 151 to output a notification image 501 together with the first execution screen 410. The notification image 501 may include information regarding a body fat measurement result, a measurement date, and a measured body part.

The notification image 501 may be output in a case in which a call is terminated or in a case in which the user views the display unit 151 (for example, a movement of the mobile terminal is sensed by the sensor unit).

According to an embodiment of the present disclosure, since body fat information of the body is measured through the first electrode unit continuously in contact with a part of the user's body and the second electrode unit in contact with other part as necessary (or while a specific function is being performed), body fat result information may be provided before the user knows it. Thus, the user does not need to bring a part of his or her body into contact with the two electrodes on purpose to receive the body fat result.

Figure 6A:
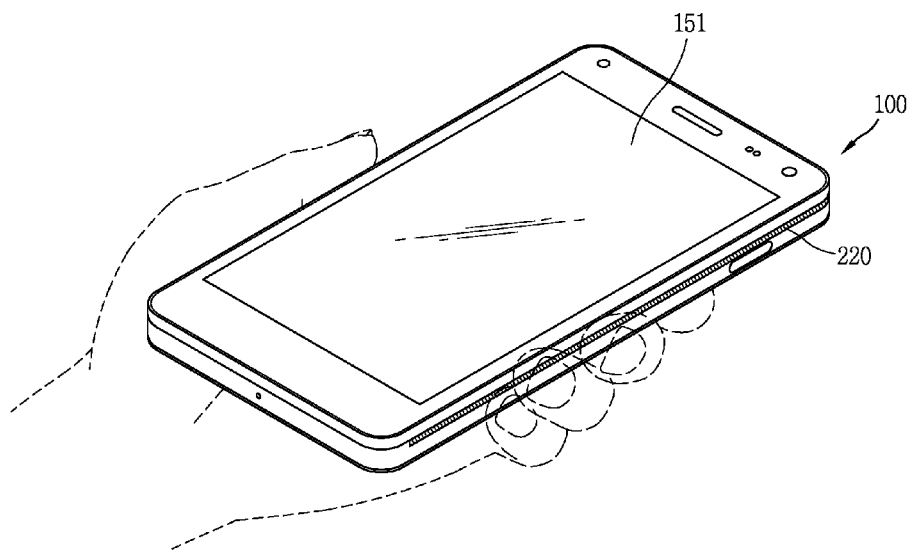
FIGS. 6A and 6B are conceptual views illustrating a mobile terminal including a second electrode unit according to various embodiments.
Figure 6B:
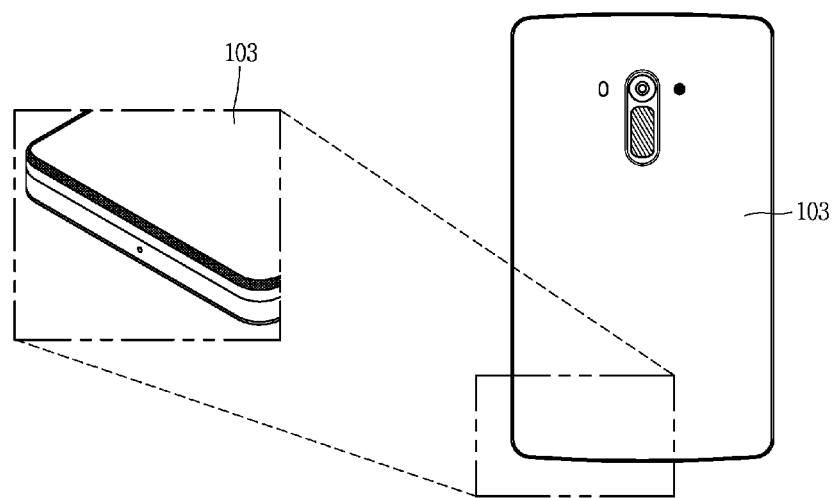

FIGS. 6A and 6B are conceptual views illustrating a mobile terminal including a second electrode unit according to various embodiments.

Referring to FIG. 6A, a second electrode unit 220 is formed on a side surface of the mobile terminal 100. The second electrode unit 220 may be formed in a region of the side surface of the mobile terminal which may be brought into contact with the user's hand when the user grips the mobile terminal. Here, both in a case in which the user wears the external device 300 (please refer to FIG. 2B) and in a case in which the user is holding the mobile terminal, the control unit 180 may form the impedance information.

Here, in a case in which a specific function is executed (for example, when a media file is played) or the display unit 151 is in a deactivated state, on the basis of a user setting, the control unit 180 may form the body fat measurement result only when the user enters a specific position.

FIG. 6B is a view illustrating a structure in which a region of the rear cover 103 of the mobile terminal 100 is formed of a metal member to form the first electrode unit. In this case, a side surface of the main body of the mobile terminal 100 may be formed as an insulator. In the case of the mobile terminal 100 according to the present embodiment, as long as the user holds the terminal body, a voltage may be measured. Since the first electrode unit is formed in a relatively wide range, body fat may be measured more frequently.

Figure 7A:
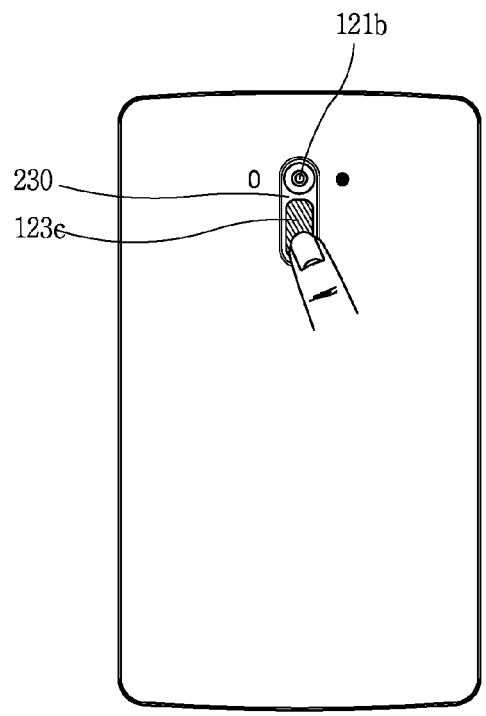
FIG. 7A is a conceptual view illustrating a mobile terminal according to another embodiment of the present disclosure.
Figure 7B:
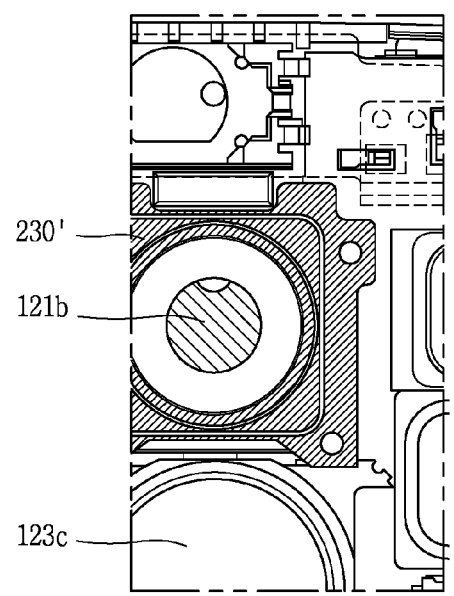
FIGS. 7B and 7C are conceptual views illustrating a structure of a rear key including a first electrode unit.
Figure 7C:
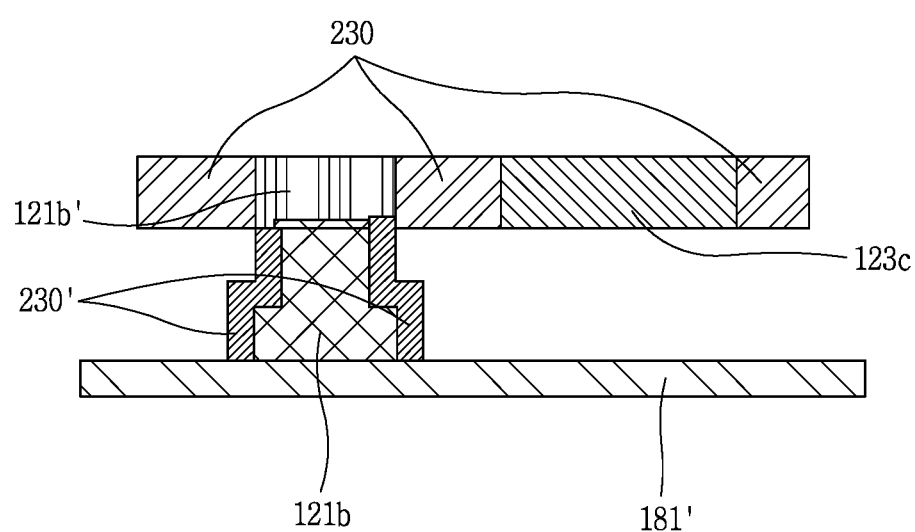

FIG. 7A is a conceptual view illustrating a mobile terminal according to another embodiment of the present disclosure, and FIGS. 7B and 7C are conceptual views illustrating a structure of a rear key including a first electrode unit.

Referring to FIGS. 7A through 7C, the second electrode unit 230 may be disposed to be adjacent to a rear key 123c and the second camera 121b. For example, the second electrode unit 230 may be a metal fixing member surrounding the rear key 123c and the second camera 121b. The second electrode unit 230 may include a first opening into which a camera window 121b' stacked on the second camera 121b is inserted and a second opening into which the rear key 123c is inserted. The rear key 123c may be a push type button forming a control command through pressing.

Referring to FIGS. 7B and 7C, A metal support portion 230' covering the second camera 121b is formed of a metal member and is electrically connected to a circuit board 181' disposed within the terminal body. The metal support portion 230' is in contact with a region of the second electrode unit 230. Thus, the outwardly exposed second electrode 230 and the circuit board 181' disposed inside the terminal body may be electrically connected to each other. Also, while the rear key 123c is being pressed, the user's finger may be in contact with the second electrode unit 230.

Alternatively, the second electrode unit 230 may be configured to cover only the rear key 123c.

While a specific function is being controlled using the rear key 123c, the control unit may obtain impedance information using the first and second electrode units 210 and 310.

Figure 8:
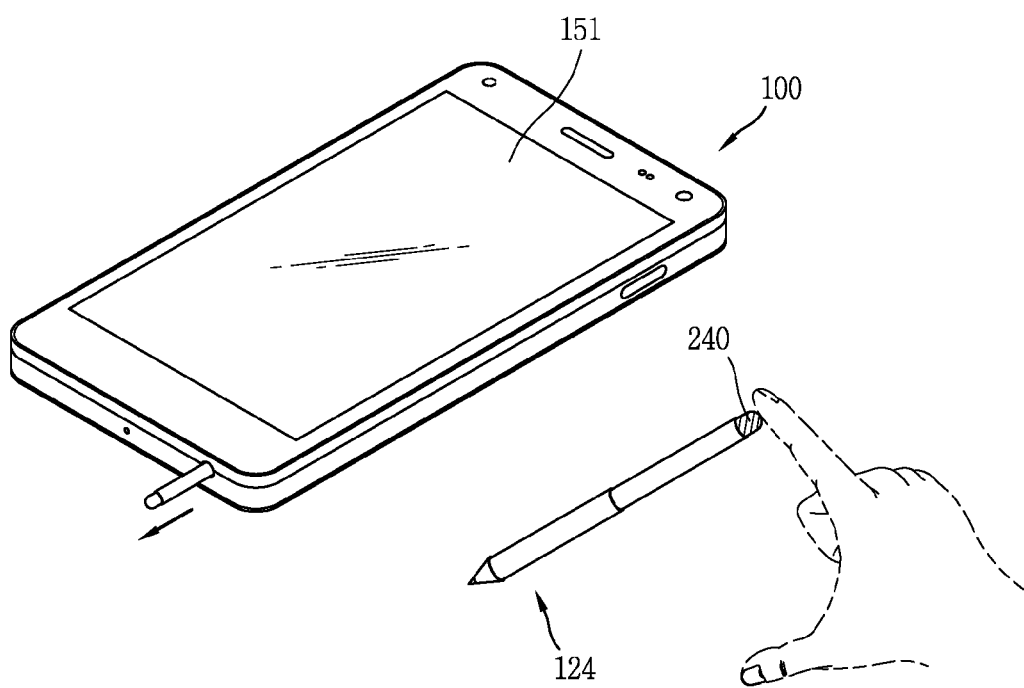
FIG. 8 is a conceptual view illustrating a structure of a second electrode unit according to another embodiment of the present disclosure.

FIG. 8 is a conceptual view illustrating a structure of a second electrode unit according to another embodiment of the present disclosure.

Referring to FIG. 8, a second electrode unit 240 is formed at one end portion of a stylus pen 124. The second electrode unit 240 may be formed at one end portion of the stylus pen 124 so as to be outwardly exposed even in a state in which the stylus pen 124 is inserted in the mobile terminal 100.

Figure 9A:
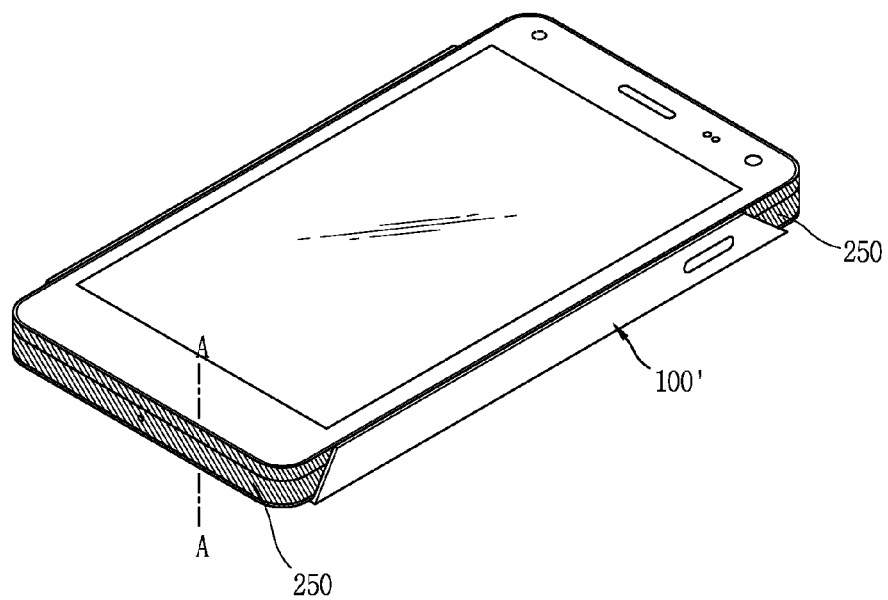
FIG. 9A is a conceptual view illustrating a structure of a second electrode unit according to another embodiment of the present disclosure.
Figure 9B:
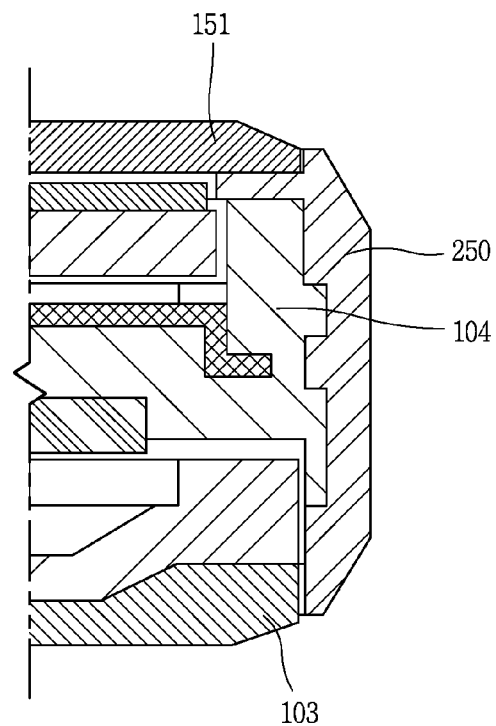
FIG. 9B is a partial cross-sectional view taken along line A-A of FIG. 9A.

FIG. 9A is a conceptual view illustrating a structure of a second electrode unit according to another embodiment of the present disclosure, and FIG. 9B is a partial cross-sectional view taken along line A-A of FIG. 9A.

Referring to FIG. 9A, the second electrode unit 250 may be formed in a region of a side surface of the mobile terminal 100. A portion of the side surface of the mobile terminal 100 may be covered by a cover 100'. In this case, the cover 100' may include an opening region such that a region of the second electrode unit 250 formed on the side surface may be exposed. The second electrode unit 250 may be formed to cover the entire side surface of the terminal body or may be formed only in a region with which the user's hand is frequently brought into contact.

Referring to FIG. 9B, the terminal body includes a mold unit 104 forming a side surface of the mobile terminal 100 and supporting the display unit 151, and the second electrode unit 250 is fixed to the mold unit 104. Although not shown specifically, the second electrode unit 250 is electrically connected to the circuit board disposed inside the terminal body.

Due to the presence of the mold unit 104, an influence of a current flowing through the second electrode unit 250 on electric elements disposed inside the terminal body may be minimized.

Figure 9C:
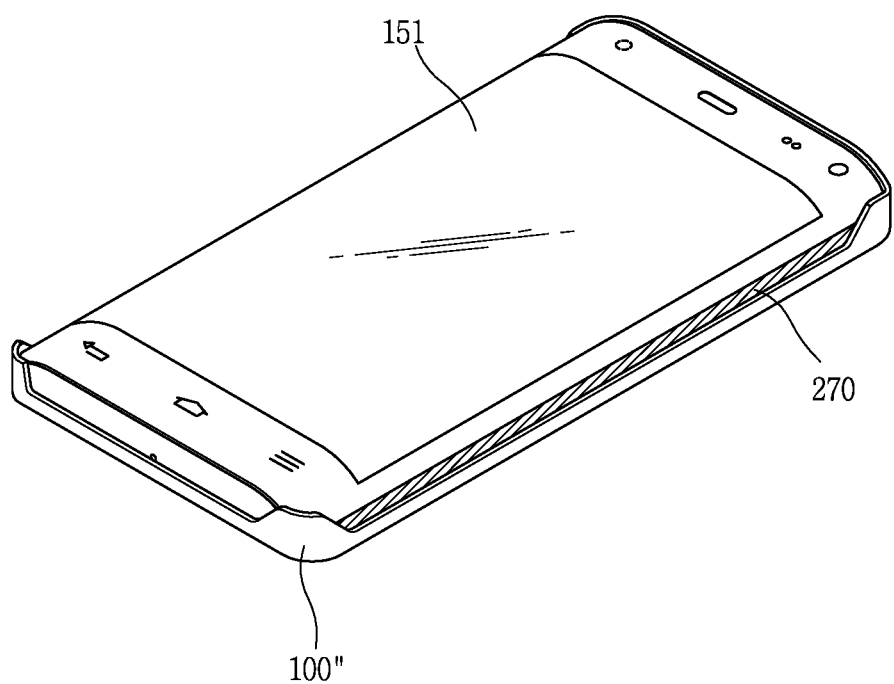
FIG. 9C is a conceptual view illustrating a structure of a second electrode unit according to another embodiment of the present disclosure.

FIG. 9C is a conceptual view illustrating a structure of a second electrode unit according to another embodiment of the present disclosure. In FIG. 9C, the display unit 151 is formed such that a region adjacent to the edge is curved. The terminal body may be formed such that a thickness thereof is reduced toward one edge. A second electrode unit 270 is formed on a side surface of the terminal body corresponding to the region.

In the present embodiment, the terminal body may be coupled to a cover 100". The cover 100" may be configured to cover a rear surface of the terminal body and cover the edge region of the terminal body. Thus, in a state in which the cover 100" is installed in the terminal body, the second electrode unit 270 disposed on the side surface of the terminal body is exposed.

In a case in which a part of the user's body comes into contact with both the first and second electrode units, the control unit 180 applies a current to measure an impedance value. However, even in the case in which a part of the body simultaneously comes into contact with the first and second electrode units, the control unit 180 may perform control to cut off supply of the current according to a user setting.

Hereinafter, a control method for providing a body fat measurement result on the basis of execution of a specific function will be described.

Figure 10:
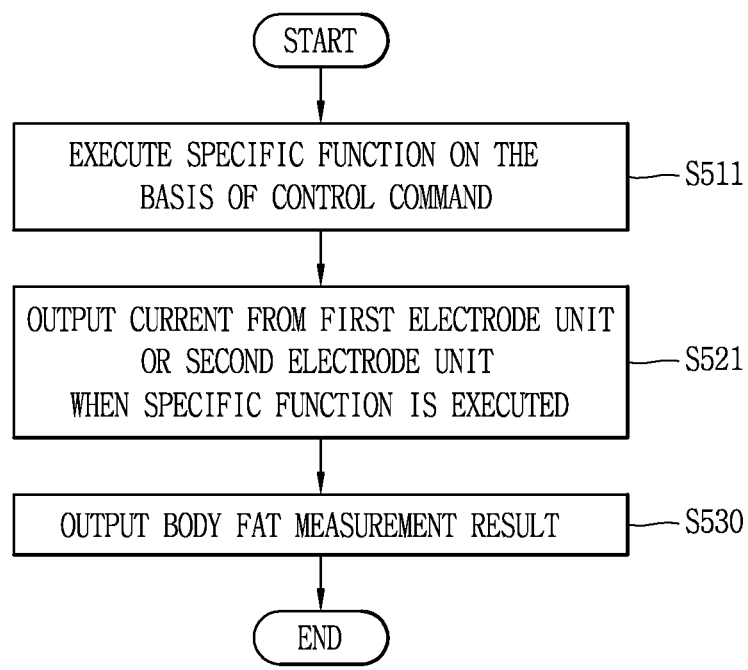
FIG. 10 is a flow chart illustrating a control method of a mobile terminal according to another embodiment of the present disclosure.

FIG. 10 is a flow chart illustrating a control method of a mobile terminal according to another embodiment of the present disclosure.

Referring to FIG. 10, when a specific function is executed on the basis of a control command (S511), a current is output from the first electrode unit or the second electrode unit (S521). The control unit 180 outputs impedance information and a body fat measurement result on the basis of the current (S530).

The control unit 180 may perform control such that the current is output while the specific function is being executed and the body fat measurement is output while the specific function is being executed. Also, while the specific function is being executed, the control unit 180 may store the body fat measurement result in the memory 170 and limit outputting thereof.

FIGS. 11A through 11D are conceptual views illustrating the control method of FIG. 4 according to various embodiments. The mobile terminal according to the present embodiment includes a second electrode unit 210 formed in a region adjacent to the first audio output unit 152a.

Figure 11A:
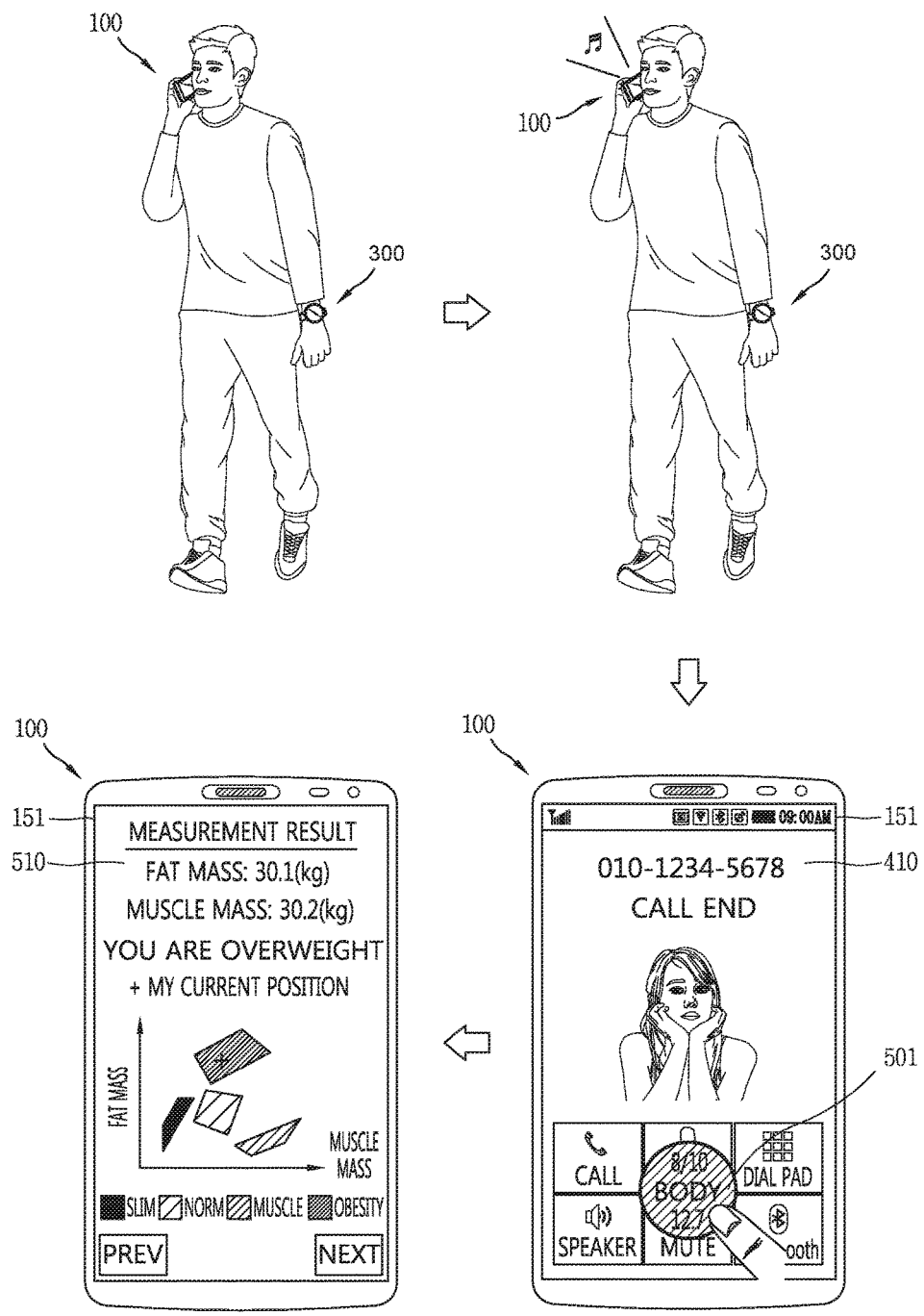
FIGS. 11A through 11D are conceptual views illustrating the control method of FIG. 4 according to various embodiments.

Referring to FIGS. 2B and 11A, when a call function is executed, the control unit 180 may control any one of the first and second electrode units 210 to output a current. The control unit 180 may form impedance information on the basis of a voltage measured while the call function is executed.

While the call function is executed, the control unit 180 may output notification information indicating that the impedance information is formed due to an output of the current. The notification information may be configured as at least one of hearing data and vibration.

That is, while the specific function is not executed, the control unit 180 does not form a voltage even a body part of the user comes into contact with the first and second electrode units 210. Alternatively, in a case in which the specific function is not executed, even though a voltage is generated between the first and second electrode units 210, the control unit 180 may not calculate the generated voltage as impedance information.

When the call function is terminated, the display unit 151 outputs a first execution screen 410 indicating termination of the call function.

Referring to FIG. 10, the control unit 180 outputs the notification image 501 on the first execution screen 410. The notification image 501 includes a body fat measurement result measured while the call function is being executed. The notification image 501 may include a measurement date (i.e., a date on which the body fat was measured), a measured body part, and body fat information, but the present disclosure is not limited thereto. For example, the notification image 501 may include an image representing a time duration in which the call function was executed and a call function.

When a touch is applied to the notification image 501, the control unit 180 executes a specific application for outputting a body fat measurement result. The display unit 151 outputs a screen information 510 of the specific application. That is, the first execution screen 410 corresponding to the first call function is switched to the screen information 510 of the specific application, and the call application may be switched to a deactivation state.

The screen information 510 of the specific application includes body information of the user. For example, the screen information 510 may include the fat mass measured by using the first electrode unit 310 and the second electrode unit 210, the muscle mass, and the result of degree of obesity calculated through the measured amounts of body fat and muscle. Although not specifically shown, the control unit 180 may apply a touch to the screen information 510 to output specific body information or additionally output body information, or the like, stored in the past.

According to the present embodiment, the user may be immediately provided with the measured body fat measurement information without having to execute a specific application for receiving the body fat measurement result on purpose. In particular, since the second electrode unit 210 is continuously in contact with the user's ear while a call function is being executed, impedance of the body may be measured while the specific function of the mobile terminal is being used.

Also, since a current is output only while a specific function allowing the second electrode unit 210 to come into contact with the user's ear is executed, power consumption may be minimized, and thus, more accurate result may be provided.

The control unit 180 perform control such that a voltage is measured only in a state in which the external device is installed in the user's body and the user is holding the mobile terminal 100, on the basis of a user setting. Also, the specific function may be executed when a call is being performed, when the user is holding the mobile terminal, or when the user is viewing video.

Figure 11B:
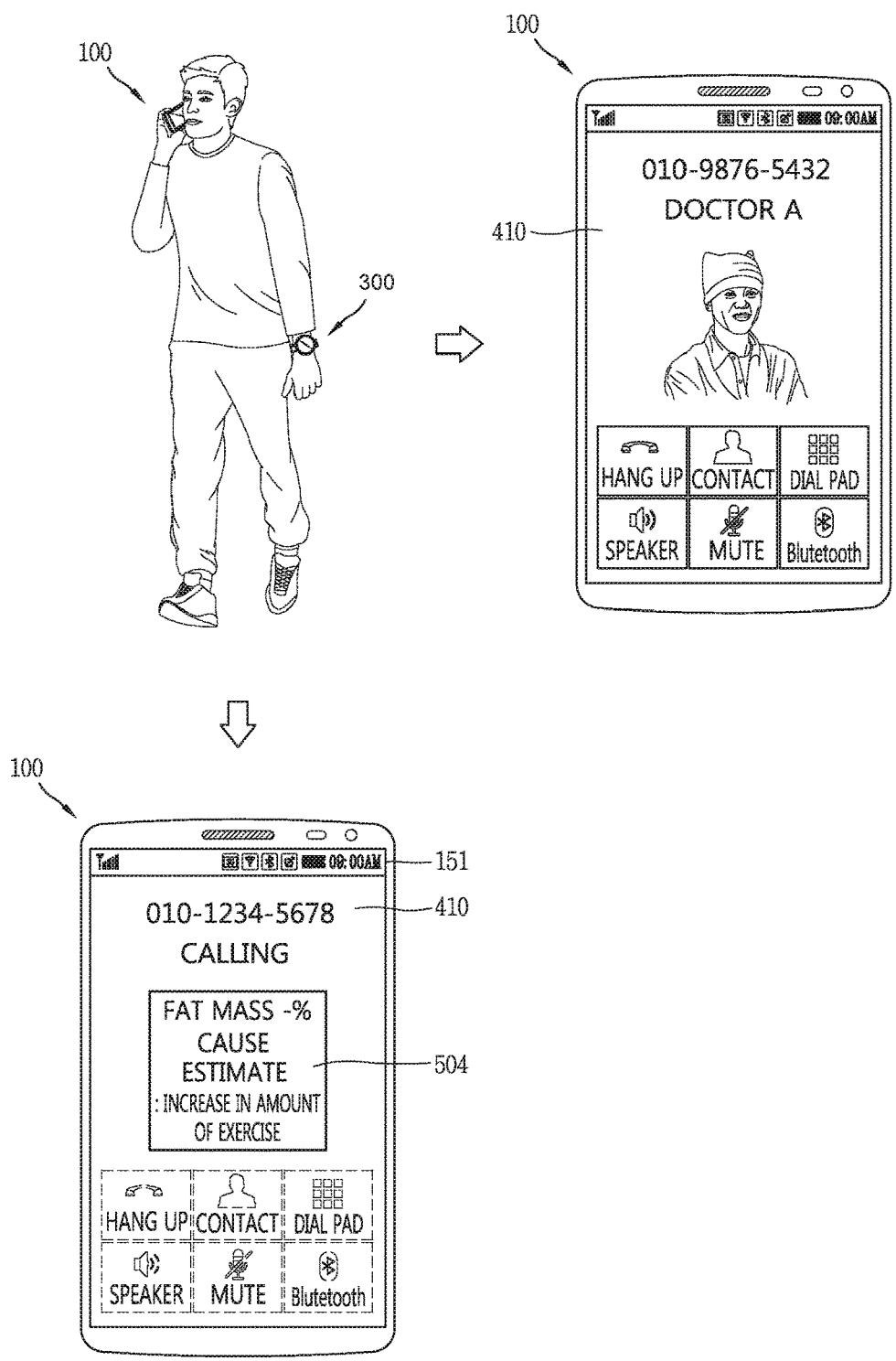

A control method for providing a body fat measurement result to the user through comparison of body fat measurement results will be described with reference to FIGS. 2B and 11B.

When the user's body comes into contact with the first and second electrode units 310 and 320, the control unit calculates body fat measurement result through impedance information. When the body fat measurement result is calculated, the control unit compares the calculated body fat measurement result with stored body fat measurement results or an average value of the body fat measurement results. In a case in which a difference between the compared measurement results is smaller than a reference value, the control unit 180 outputs the first execution screen 410. In this case, the control unit interrupts outputting of a notification regarding a stage in which a voltage is measured or a notification regarding the body fat measurement result.

In a case in which the a difference between the compared measurement results is equal to or greater than the reference value, the control unit 180 collects information which has caused the different to be equal to or greater than the reference value. For example, the control unit 180 may analyze the cause of the difference through information regarding an amount of exercise of the user, food intake information and recorded by the user, or information regarding sleeping hours measured by the sensor of the mobile terminal 100 or information regarding an amount of exercise of the user or information regarding sleeping hours measured by the external device 300.

The body fat measurement result 504 is output on the first execution screen 410. The body fat measurement result 504 may include a fat mass, a changed fat mass, a reason of the change in the fat mass, and guide information for achieving a target fat mass.

According to the present embodiment, the fat mass may be measured even though the user does not intend to do so, and the measurement result may be output only when the result is required to be recognized by the user, namely, when the body fat measurement result has been greatly changed. Thus, the user may frequently store the body measurement result and, if necessary, the user may check the body measurement result.

Figure 11C:
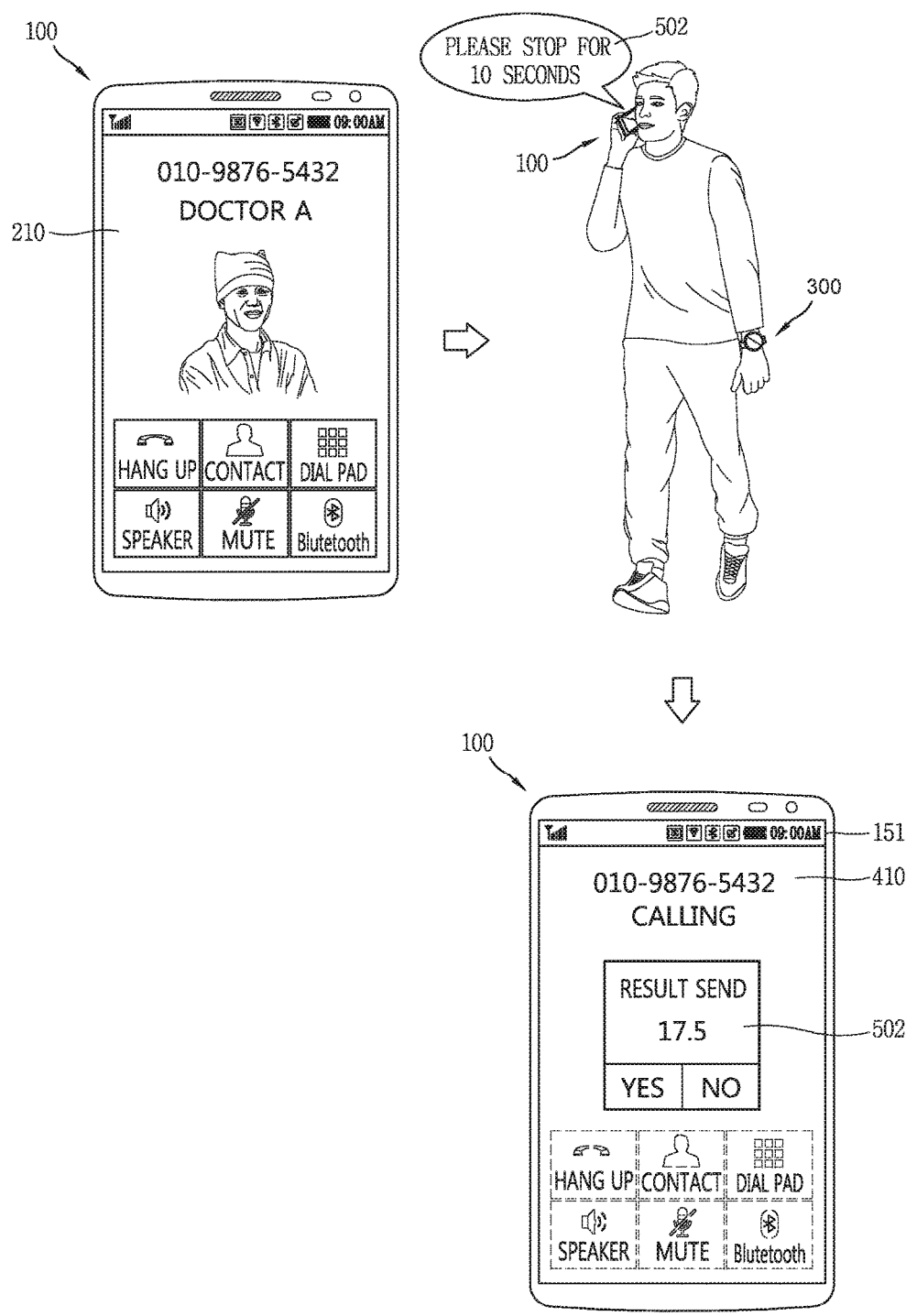

A control method of the body fat measurement function when a call function is executed with a specific external terminal will be described with reference to FIGS. 2B and 11C. In a case in which a call function is performed with the specific external terminal, the control unit 180 controls the first electrode unit 310 or the second electrode unit 210 to output a current. In a case in which the call function is performed with an external terminal other than the specific external terminal, the control unit 180 may not output a current or may not form impedance information by a formed voltage.

When a voltage is generated between the first and second electrode units 310 and 210, the control unit 180 may output guide information 502 for more accurate measurement. For example, the guide information 502 may be a voice guide such as "please stop for ten seconds". Upon hearing the guide information, the user may minimize a movement to obtain more accurate impedance information.

While the call function is being executed, the control unit 180 may control the display unit 15 to output the measured body fat measurement result 502. The body fat measurement result window 502 may be output together with the first execution screen 410 of the call application. Alternatively, the control unit 180 may control the display unit 151 to output the body fat measurement result window 502 after the call function is terminated.

The body fat measurement result window 502 may include a graphic image for checking whether to transmit the body fat measurement result to the specific external terminal. On the basis of a user selection, the control unit 180 controls the wireless communication unit 110 to transmit the body fat measurement result to the specific external terminal.

Alternatively, the control unit 180 may control the wireless communication unit 110 to transmit the body fat measurement result to the specific external terminal while the call function is being performed. Accordingly, the user of the external terminal may continue to call communication with the user by using the received body fat measurement result.

According to the present embodiment, since the user's body measurement information is transmitted to the external terminal in real time, more accurate result may be provided to a counterpart who needs the user's body measurement information, in real time. For example, the user of the external terminal may be a doctor who takes care of the user.

Figure 11D:
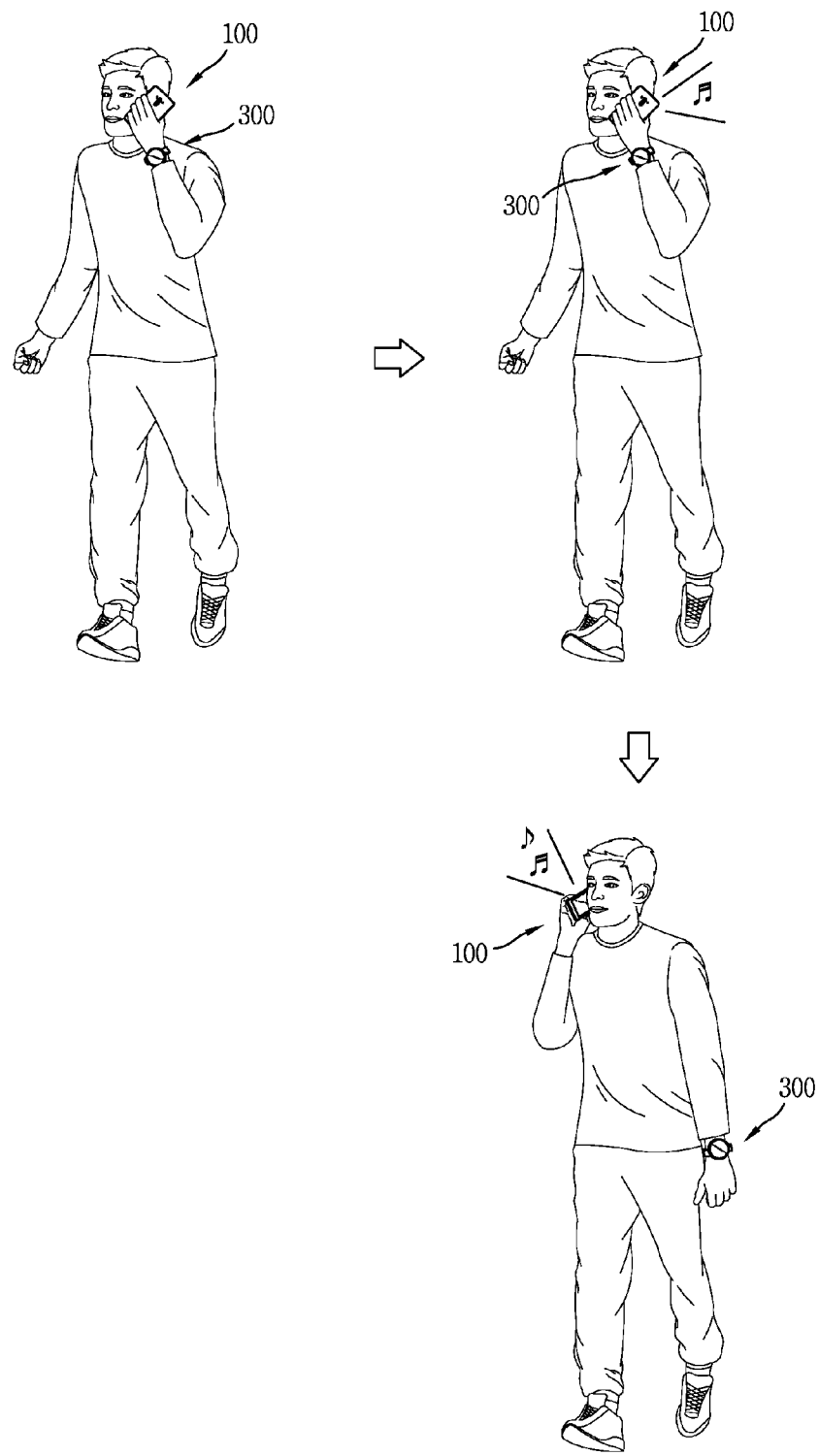

A control method for measuring each of body parts of the user will be described with reference to FIGS. 2B and 11D. While a call function is being executed, the control unit 180 outputs a current and calculates a body fat measurement result on the basis of a difference in voltage between the first and second electrode units 310 and 210.

When a body fat measurement result of a measurable first body part is calculated in a state in which the second electrode unit 210 provided in the mobile terminal 100 is in contact with a part of the user's body, the control unit 180 may output guide information to move the position of the second electrode unit 210. The guide information may be configured as voice data.

While the call function is being executed, the second electrode unit 210 disposed to be adjacent to the first audio output unit 152a is positioned to be in contact with any one of both ears of the user. For example, when the user wears the external device 300 on his or her left wrist and the second electrode unit 210 is in contact with the left ear, the control unit 180 outputs the guide information.

Accordingly, when the second electrode unit 210 is in contact with the right ear, the control unit 180 may obtain impedance information regarding the entire body.

According to the present embodiment, while the call function is being performed, the second electrode unit 210 may be brought into contact with both ears or to a ear advantageous for measuring body fat in the entire body of the user, thus providing a body fat measurement result of an expanded region.

Figure 12A:
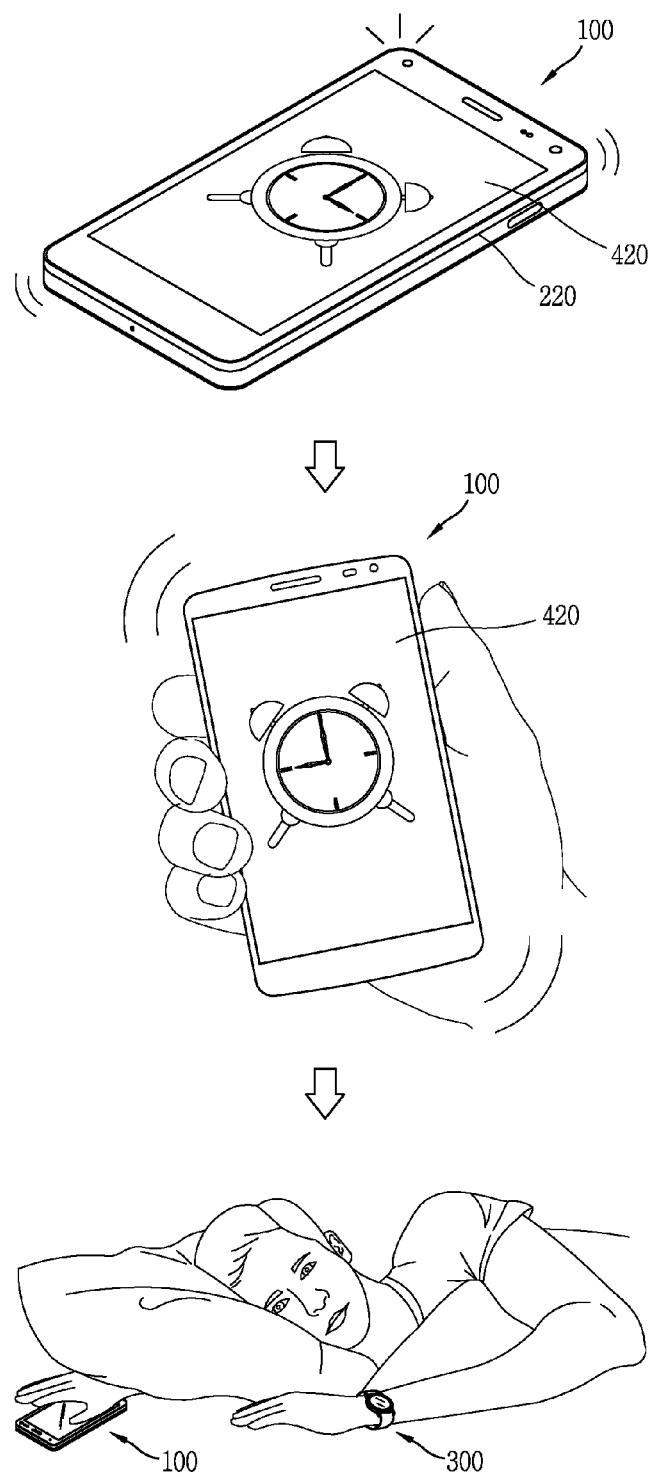
FIGS. 12A through 12C are conceptual views illustrating a control method for providing a body fat measurement result while a specific function is being executed according to another embodiment of the present disclosure.
Figure 12B:
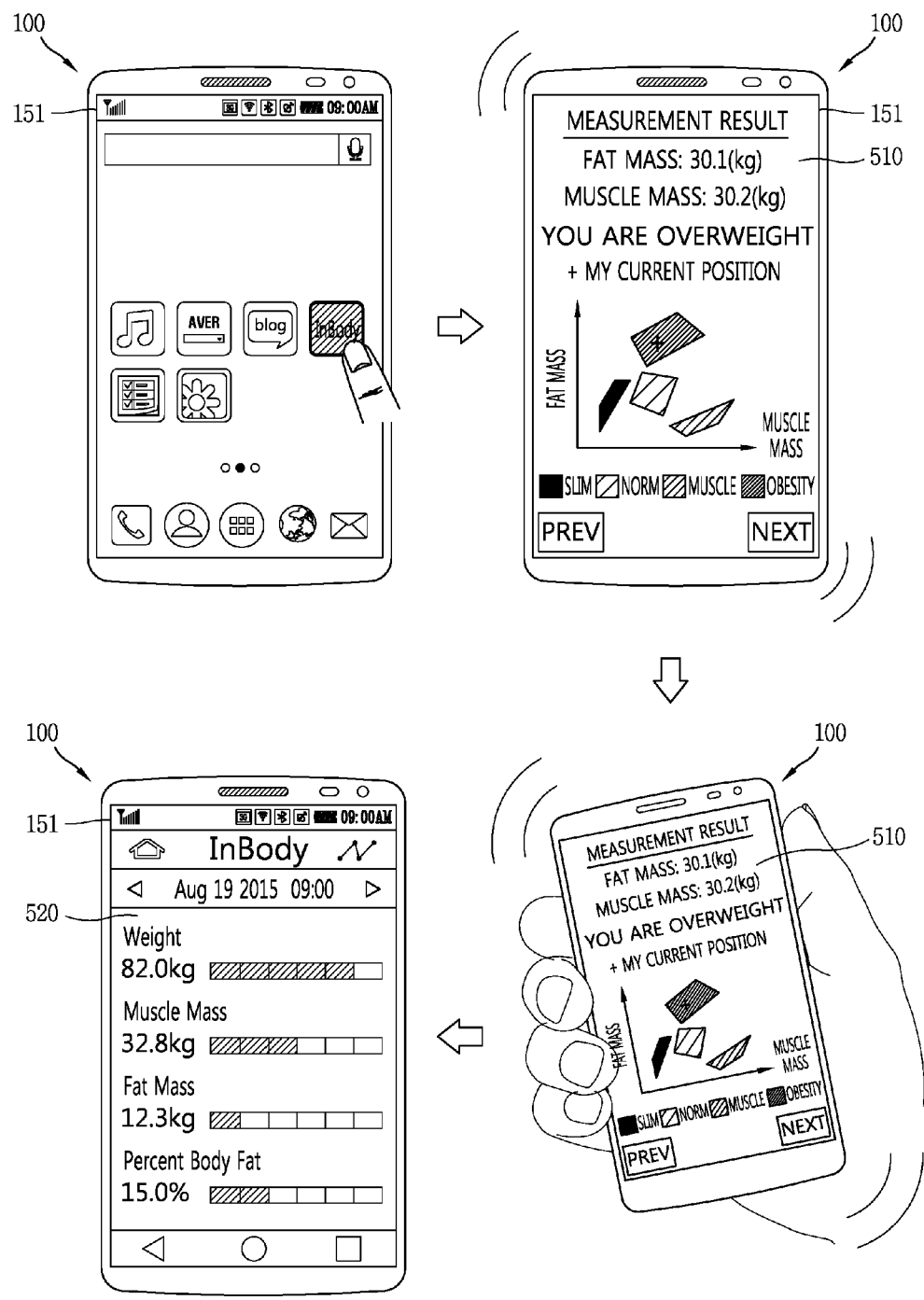
Figure 12C:
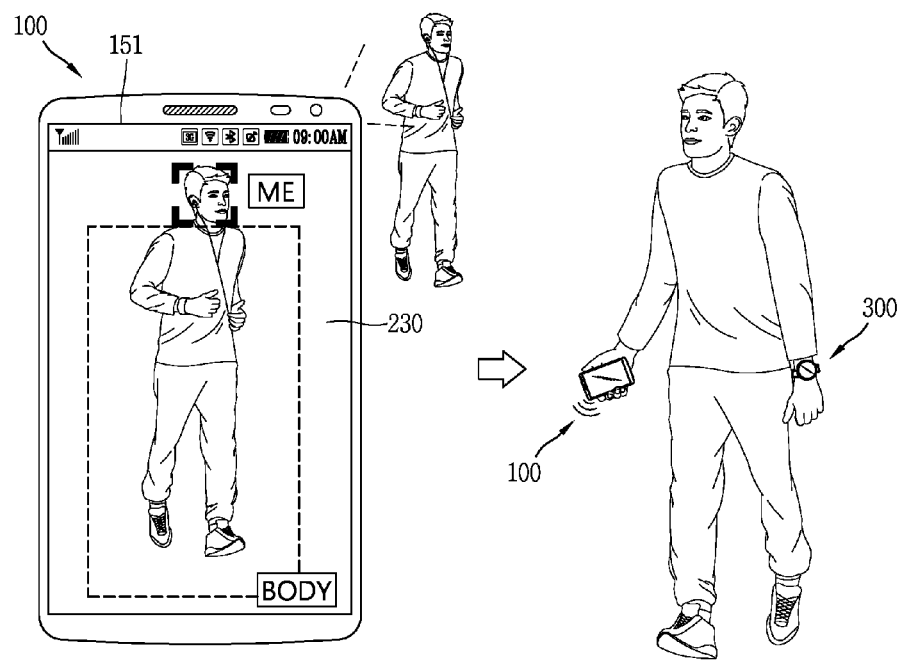
Figure 12C:
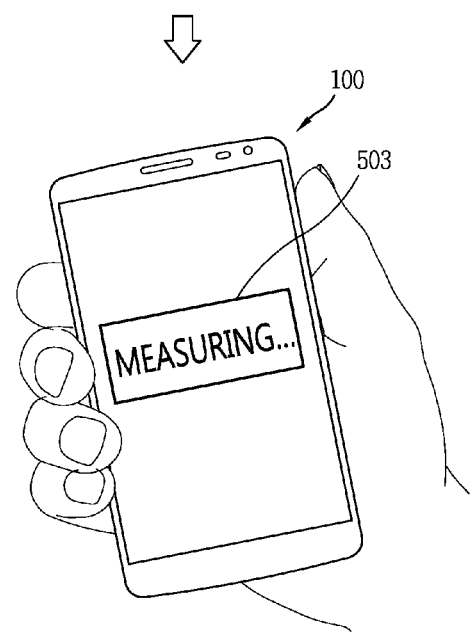

FIGS. 12A through 12C are conceptual views illustrating a control method for providing a body fat measurement result while a specific function is being executed according to another embodiment of the present disclosure. The mobile terminal according to the present embodiment includes a second electrode unit 220 formed on a side surface of the terminal body.

Referring to FIGS. 7A and 12A, when an alarm application is executed and alarm information is output, the control unit 180 may form the body fat measurement result. For example, the alarm application is activated by the user at a preset time. When the alarm application is activated, the display unit 151 may output a second execution screen 420, the audio output unit 152 may output an alarm sound, or vibration may be generated by the haptic module 153.

When the alarm application is activated, the control unit 180 outputs a current by using the first electrode unit or the second electrode unit. Alternatively, when the alarm application is not activated, even though a voltage is generated by the first and second electrode units, the control unit 180 may not form the voltage as a body fat measurement result.

While a control command for controlling the output alarm information is applied, when a part of the user's body comes into contact with the second electrode unit 220, the control unit 180 forms the body fat measurement result. The control unit 180 may output guide information instructing the user to bring his or her body part into contact with the second electrode unit 220 together with the alarm information.

For example, the control unit 180 may output the guide information (hearing data or vibration) until before the body fat measurement result is formed.

According to the present embodiment, alarm information may be output at a time previously set by the user to output the alarm information, to inform the user about the time, and the body fat measurement result may be output. For example, in a case in which the user gets up by the alarm information, a body fat measurement result measured at the time when the user gets up may be regularly collected.

A control method for outputting a current on the basis of execution of an application for providing the body fat measurement result will be described with reference to FIGS. 7A and 12B. On the basis of a touch applied to an icon, or the like, corresponding to the specific application, the control unit 180 executes the specific application and outputs the screen information 510.

The screen information may include various types of information according to previously collected body fat measurement result. For example, a fat mass, a muscle mass, and information according to a degree of obesity are output.

On the basis of the control command (the touch applied to the icon) from the user, the control unit 180 outputs a current by using the first electrode unit or the second electrode unit 220 while the specific application is being executed. Alternatively, in a case in which the alarm application is not activated, even though a voltage is generated by the first and second electrode units, the control unit 180 may not form the voltage as a body fat measurement result. While the body fat measurement result is obtained, the control unit 180 may output guide information for the body part to continuously come into contact with the second electrode unit 220.

When the body fat measurement result is formed on the basis of the voltage generated between the first and second electrode units, the control unit 180 switches the first screen information 510 into second screen information 520. The second screen information 520 may include immediately previously formed body fat measurement result.

According to the present embodiment, when an application for checking the body fat measurement result is executed according to a user intention, impedance of the body may be measured in real time and an updated body fat measurement result may be provided.

Referring to FIGS. 7A and 12C, after an image of a subject recognized as the user of the mobile terminal 100 is captured by the camera 121 or after an image of a part of the user's body is captured by the camera 121, when a part of the body comes into contact with the second electrode unit 220, the control unit 180 forms a body fat measurement result on the basis of the measured impedance information.

In a case in which an image of the user is captured, the control unit 180 may control the memory unit 170 to store a body fat measurement result collected thereafter together with the captured image. Although not specifically shown in the drawings, the control unit 810 may control the display unit 151 to output the captured user image to the body fat measurement result.

Accordingly, the user may be provided with a fat mass measured whenever his or her face is imaged, together with a picture, and thus, the user may recognize his or her face together with numerical body measurement values.

Figure 13:
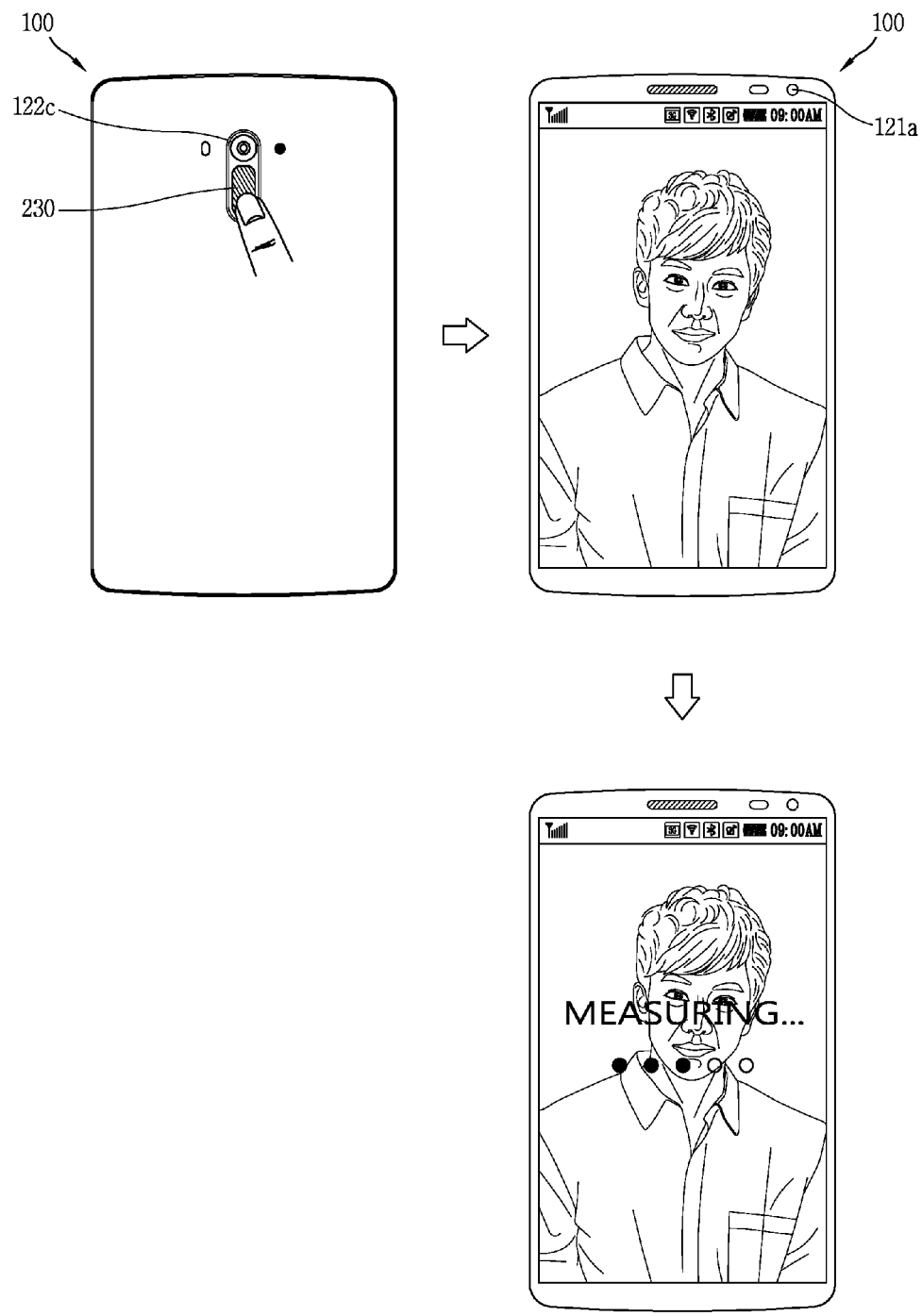
FIG. 13 is a conceptual view illustrating a control method for forming a body fat measurement result according to another embodiment of the present disclosure.

FIG. 13 is a conceptual view illustrating a control method for forming a body fat measurement result according to another embodiment of the present disclosure. Referring to FIGS. 4B and 8, the control unit 180 may control the front camera 121a on the basis of a control command applied to the rear key 122c. That is, the control unit 180 may capture a face of the user by using the rear key 122c.

In a case in which the user's face is sensed by the front camera 121, the control unit 180 may output a current between the first and second electrode units to obtain impedance information.

In a case in which an image of the user is obtained (that is, when image capturing is performed) by the front camera 121a, the control unit 180 obtains impedance information using a voltage between the second electrode unit 230 adjacent to the rear key 122c and the first electrode unit of the external device. In a case in which the front camera 121a is activated, when the user's face is sensed by the front camera 121, the control unit 180 may control the first electrode unit or the second electrode unit to output a current.

Alternatively, in a case in which the user's face is sensed by the front camera 121a, the control unit 180 may output electric power, and control the display unit 151 to output guide information. That is, the guide information may be output on a preview image obtained by the camera 121. on the basis of the guide information, the user may maintain the state in which the user's hand is in contact with the second electrode unit 230, and perform image capturing.

In this case, the control unit 180 may control the memory 170 to store the formed body fat measurement result together with the captured user's face image. Accordingly, the user may be provided with the body fat measurement result together with the captured image.

Figure 14A:
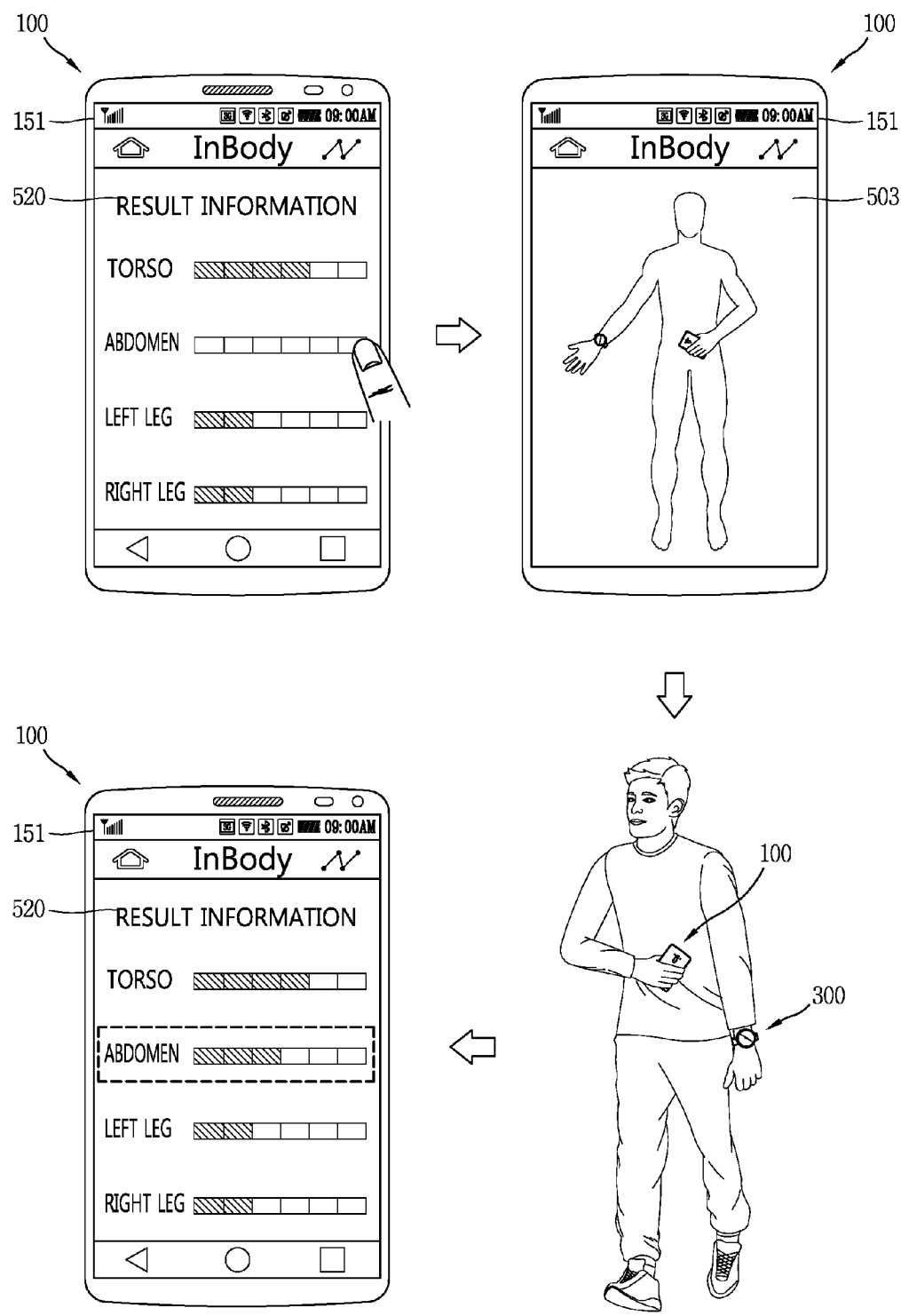
FIGS. 14A and 14B are conceptual views illustrating a control method for obtaining a result of measuring body fat of a desired body part.
Figure 14B:
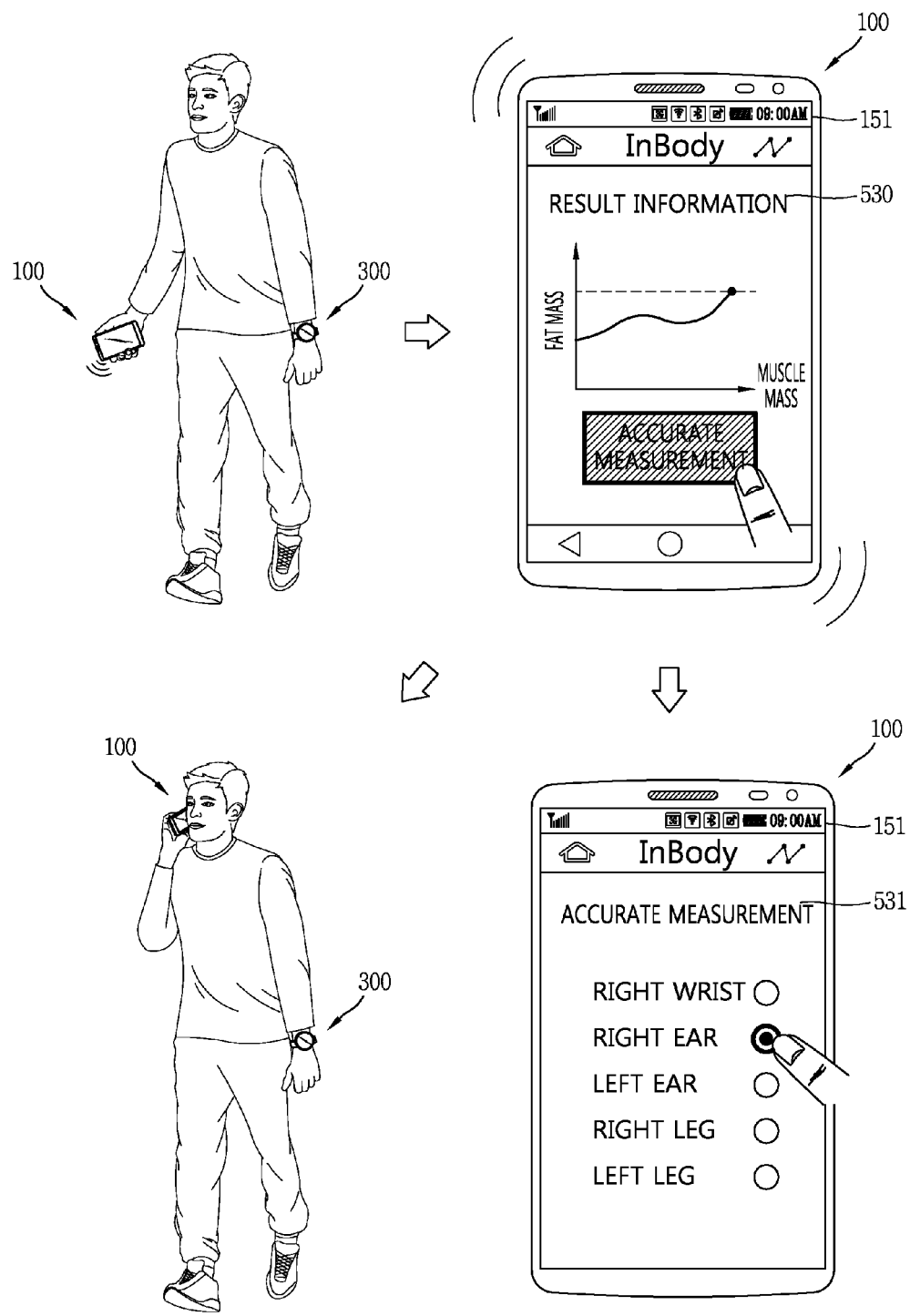

FIGS. 14A and 14B are conceptual views illustrating a control method for obtaining a result of measuring body fat of a desired body part.

Referring to FIG. 14A, when the specific application is executed, the display unit 151 outputs second screen information 520. The second screen information 520 may include body fat information measured for each body parts. The control unit 180 may select a body part on the basis of a touch applied to the second screen information 520. The control unit 180 controls the display unit 151 to output guide information 503 for measuring body fat of the selected body part.

For example, the guide screen 503 may include an image indicating positions of the first and second electrode units. The control unit 180 forms a body fat measurement result on the basis of a voltage sensed after the guide screen 503 is output. On the basis of the sensor unit for sensing a movement, the control unit 180 may determine whether the second electrode unit is placed at an accurate position.

When the body fat measurement result is formed, the control unit 180 controls the display unit 151 to output the body fat measurement result on the second screen information 520 together.

According to the present embodiment, the user may bring the mobile terminal into contact with a specific body part to form a body fat measurement result of the desired body part.

That is, the control unit 180 may divide the body into segments and measure a fat mass and a muscle mass of each of the segments. That is, in a case in which the user is curious about a change in a fat mass of a certain body part, the control unit 180 may provide this.

A control method for guiding re-measurement by using a body fat measurement result will be described with reference to FIG. 14B. The control unit 180 measure body fat by using the first and second electrode units and stores the measured body fat in the memory 170. In a case in which the body fat measurement result exceeds a limit value set by the user, the control unit 180 executes the specific application and outputs guide information for guiding re-measurement. The display unit 151 may output the guide information on third screen information 530 of the application.

For example, the limit value may be a numerical value set by the user or may be a numerical value in consideration of a user's physical condition. The limit value corresponds to a fat mass, but the present disclosure is not limited thereto.

When a touch is applied to the guide information output on the third screen information 530, the control unit 108 control the display unit 151 to output a measurement control screen 531 for selecting a body part. For example, the control screen 531 may display parts that may be contacted by the second electrode unit of the mobile terminal 100. When a part is selected, the control unit 180 may measure a voltage between the first and second electrode units and form impedance information. The control unit 180 may store the impedance information together with the selected measurement part information.

Accordingly, in a case in which the body measurement value exceeds a preset reference value, the user may accurately perform measurement on each of the body parts. Alternatively, when the body measurement value exceeds the reference value, the user may recognize it immediately.

Figure 15A:
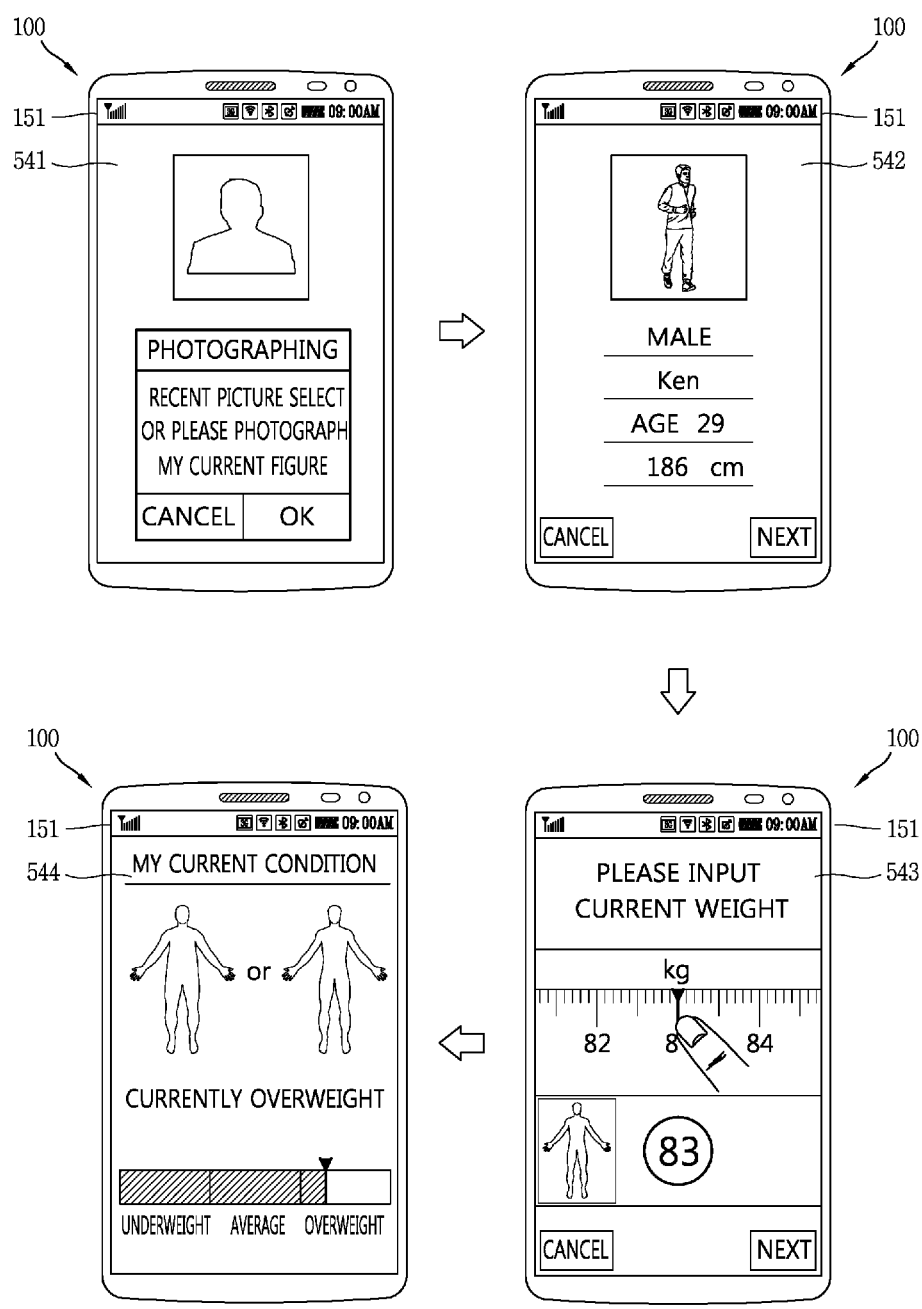
FIGS. 15A and 15B are conceptual views illustrating a control method for providing a body fat measurement result measured by the first and second electrode units.
Figure 15B:
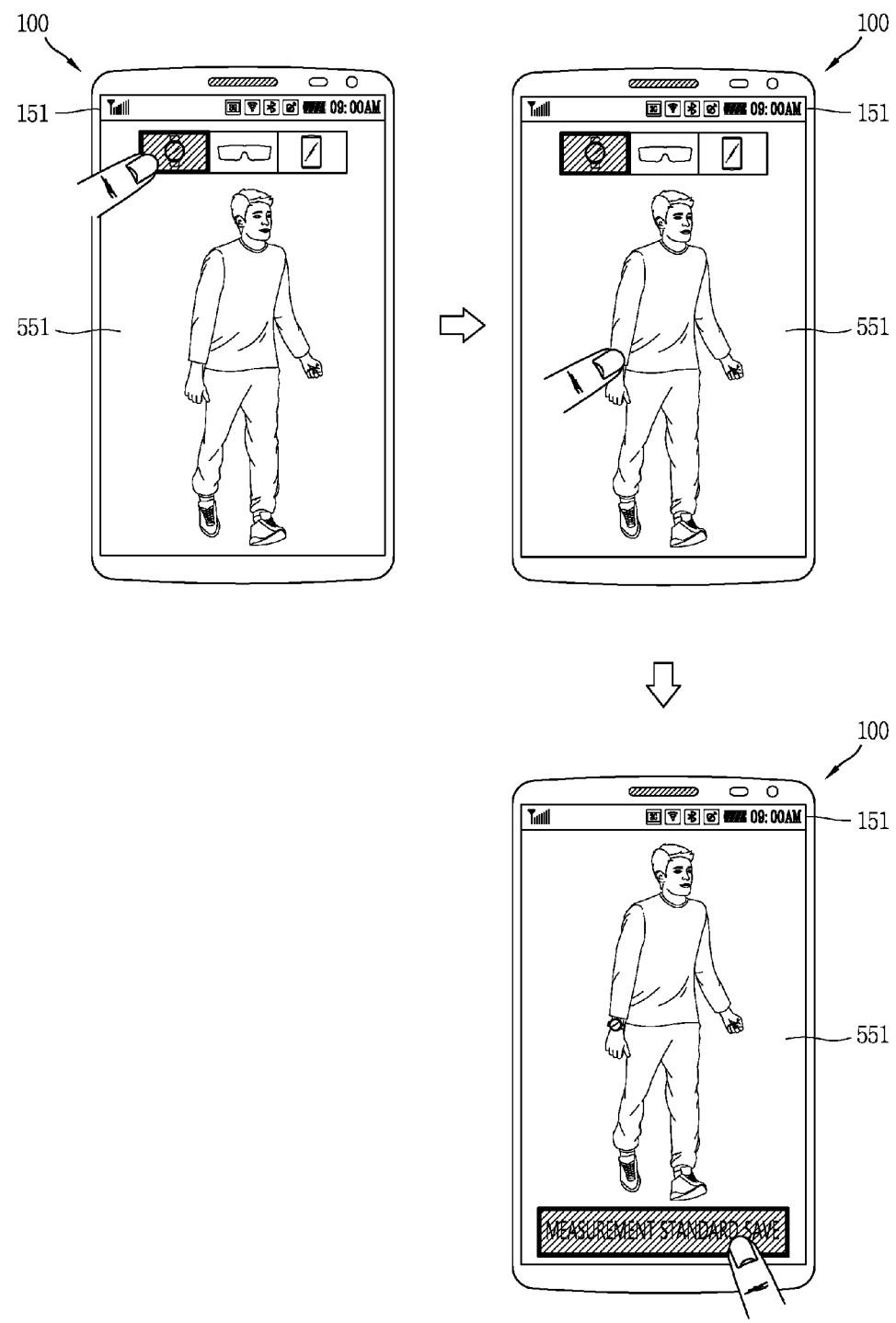

FIGS. 15A and 15B are conceptual views illustrating a control method for providing a body fat measurement result measured by the first and second electrode units. In these exemplary embodiment, in a case in which the application is executed on the basis of a control method input by the user or in a case in which user impedance information is formed by the first and second electrode units, the control unit 180 controls the display unit 151 to output an execution screen of the application.

A control method for storing user's body information will be described with reference to FIG. 15A. In a case in which the application is first executed, impedance information of the user is formed, but body information for forming a body fat measurement result is insufficient, the control unit 180 may output an execution screen for receiving body information.

The display unit 151 outputs first screen information 541 for inputting a user image. The control unit 180 may activate the camera 121 on the basis of a touch applied to the first screen information 541.

A second execution screen 542 may include an input window allowing for inputting body information including a gender, a name, an age, and a height. The second execution screen 542 may include a user image input in the first execution screen 541.

A third execution screen 543 may include a graphic image for inputting a weight of the user. The third execution screen 543 may include an input window for inputting weight information as text.

The first to third execution screens 541, 542, and 543 may be sequentially output, and the order of outputting the first to third execution screens 541, 542, and 543 is not limited to that illustrated in FIG. 15A.

A fourth execution screen 544 includes a body fat measurement result formed using the input body information and the impedance information of the body. The body fat measurement result may include a numerical value of body fat, a body condition evaluation result (information regarding obesity information), and a body condition.

A control method for setting a position where the external device including the first electrode unit is to be worn will be described with reference to FIG. 15B. The display unit 151 outputs a setting screen 551, and the setting screen includes an image displaying a user's body and an icon corresponding to at least one external device.

The external device may be a device which was previously wirelessly connected to the mobile terminal 100, but the present disclosure is not limited thereto. That is, the external device may be set first and then wirelessly connected to the mobile terminal. In a case in which the external device is mounted on a body, the external device may be a wearable device including a first electrode unit which is to come into contact with the body, or may be any other mobile terminal.

The control unit 180 may set a region of the body where the external device is to be worn on the basis of a touch applied to the icon or the image. Accordingly, a part of the body with which the second electrode unit may be brought into contact may be determined.

In a case in which a voltage is generated in the first and second electrode units, the control unit 180 may recognize a part of the body with which the second electrode unit is brought into contact, and thus, the part of the body in which impedance information was measured may be more accurately recognized.

Figure 16A:
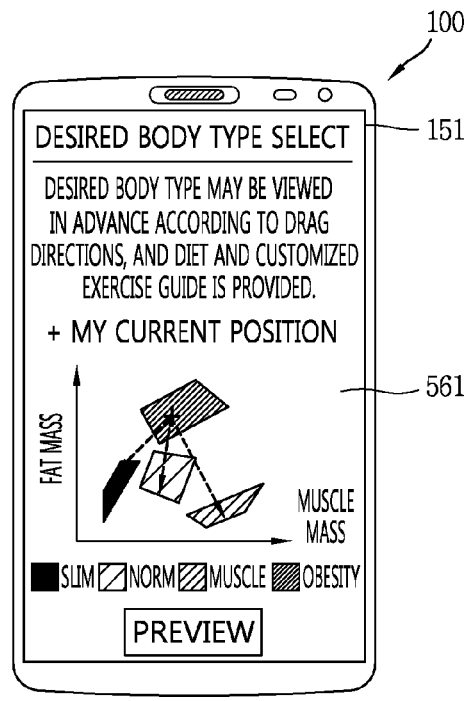
FIGS. 16A through 16C are conceptual views illustrating a control method for providing a body fat measurement result according to another embodiment of the present disclosure.
Figure 16A:
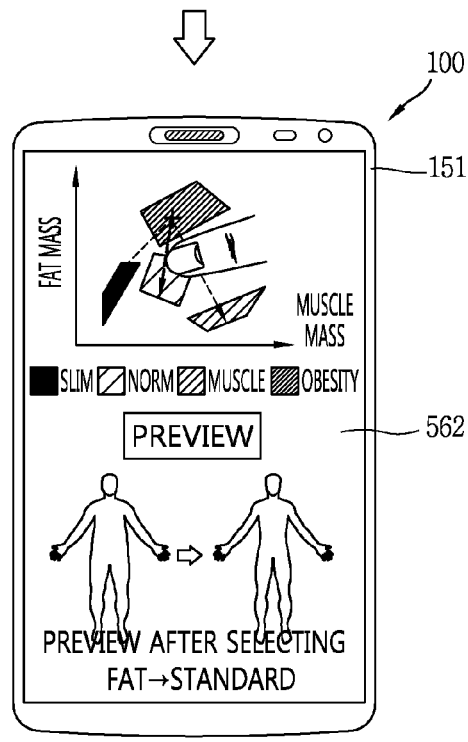
Figure 16B:
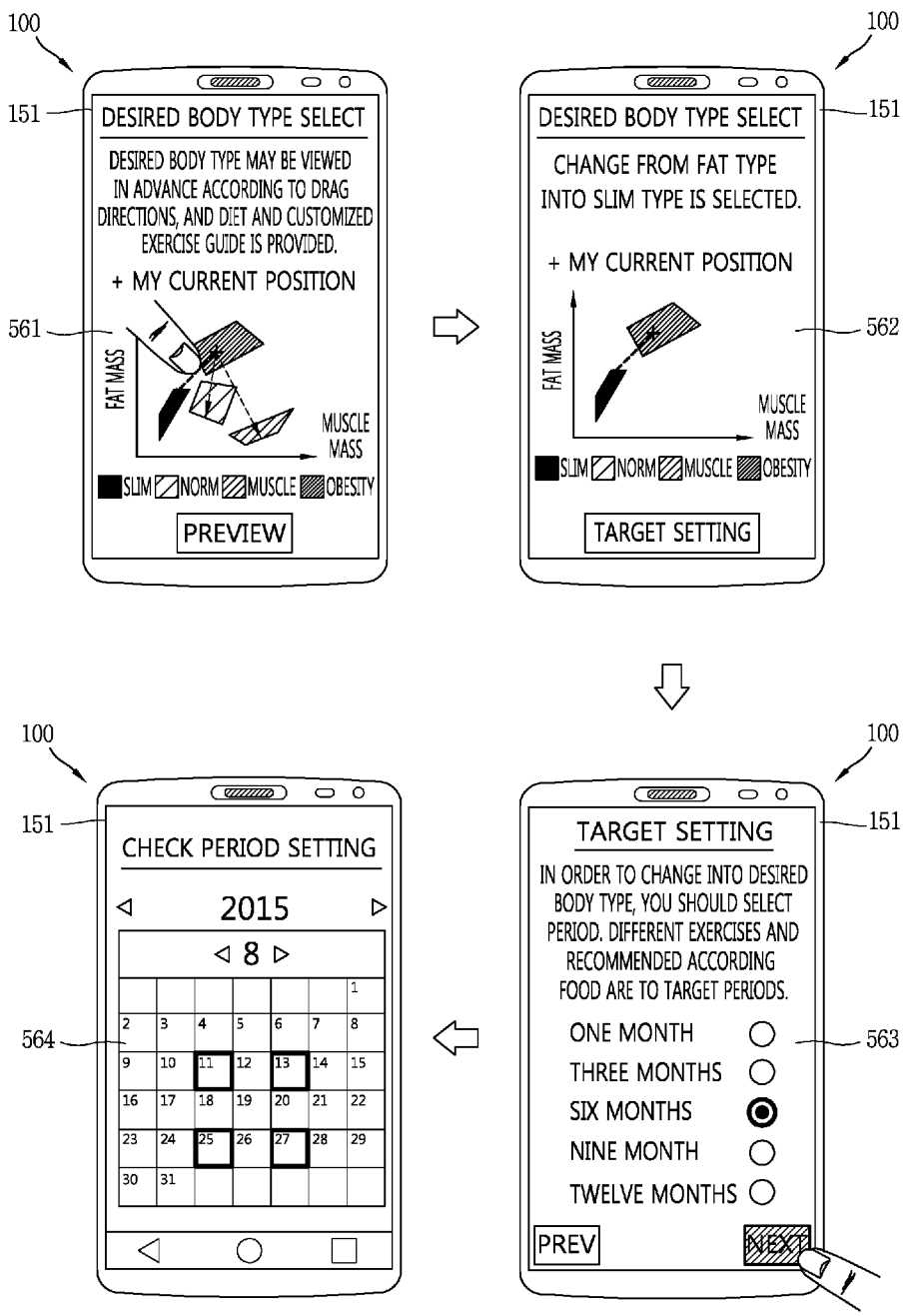
Figure 16C:
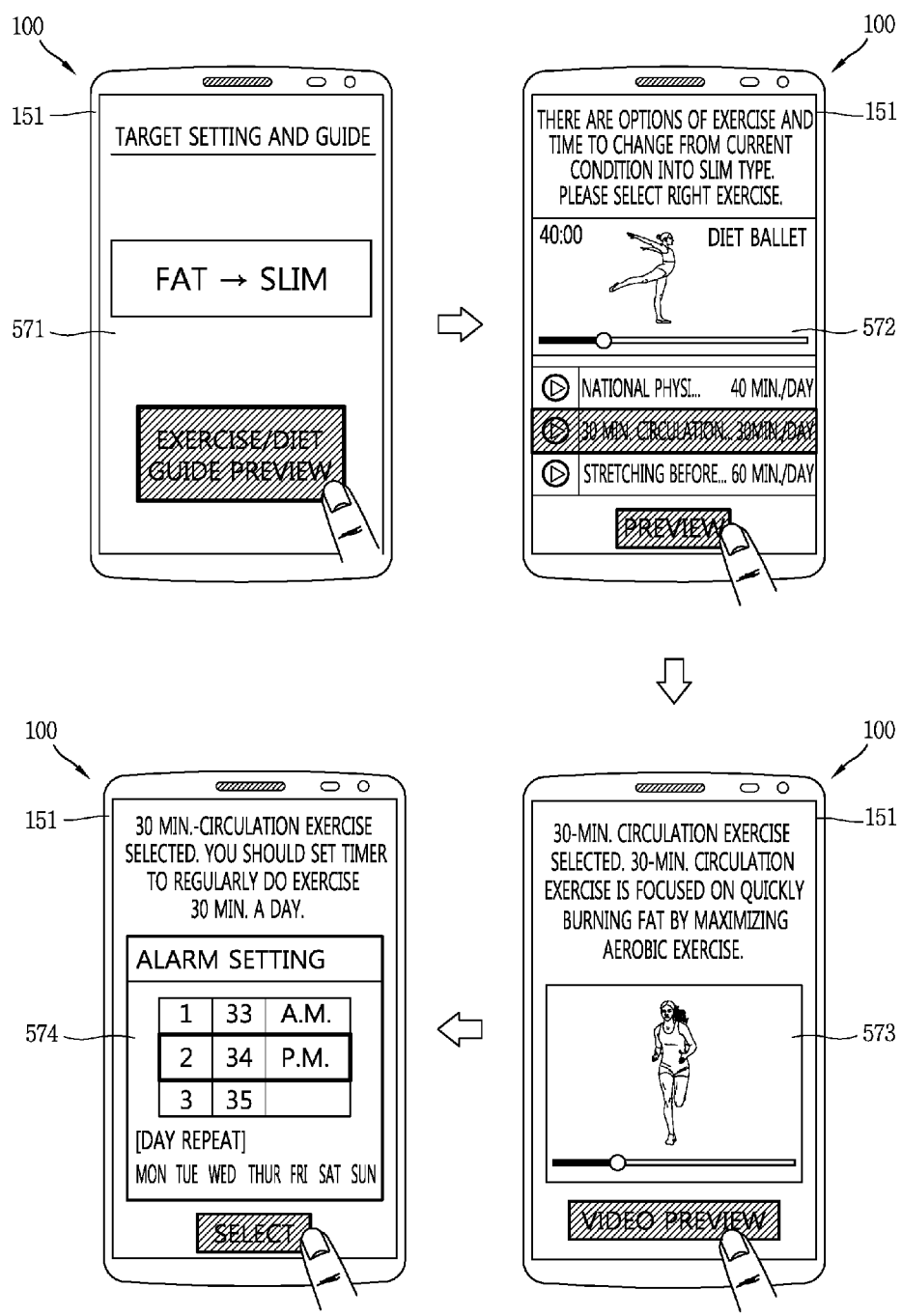

FIGS. 16A through 16C are conceptual views illustrating a control method for providing a body fat measurement result according to another embodiment of the present disclosure.

Referring to FIG. 16A, the control unit 180 outputs a first result screen 561 using the formed body fat measurement result. For example, the first result screen 561 may include an image displaying a body fat measurement result of the user in a graph illustrating a fat mass over a muscle mass.

Also, the control unit 180 may set a target fat mass of the user on the basis of a touch applied to the graph. When the target fat mass is set, the control unit 180 outputs a second result screen 562. The second result screen 552 may include a body condition image displaying the current target fat mass of the user and a body condition image representing the set target fat mass.

However, the information included in the second result screen 562 is not limited thereto. For example, the second result screen 562 may include guide information including an amount of exercise or an amount of food for achieving the target fat mass.

The control unit 180 analyzes whether a changed body fat measurement result has resulted from doing exercise or has resulted from taking low-calorie food, and output corresponding result data.

Referring to FIG. 16B, when the target fat mass is set, the control unit 180 may control the display unit 151 to output a third result screen 563 for setting a target period. The third result screen 563 may include a graphic image for selecting a target period, and the control unit 180 may form guide information regarding a recommended exercise or recommended food by using the body fat measurement result, the target fat mass, and the target period.

The control unit 180 outputs a fourth result screen 564 for setting a period of body fat measurement. The fourth result screen 564 may be a calendar image, and the user may designate a date for performing body fat measurement by applying a touch.

The control unit 180 may set a recommended measurement date in advance on the basis of the body fat measurement result, the target fat mass, and the target period.

When the measurement date is set, even though the user does not applies a specific control command, the control unit 180 may store a body fat measurement result measured before the user knows it, and compares the measured body fat measurement result with the target body fat to form new guide information. Also, the control unit 180 may output guide information indicating measurement of body fat on the set measurement date.

A control method for providing guide data set on the basis of the body fat measurement result will be described with reference to FIG. 16C. The control unit 180 forms guide data on the basis of the set target body fat and the body fat measurement information.

In a case in which there is no target fat mass or a target body, the display unit 151 outputs a first guide screen 571. The first guide screen 571 may include a graphic image for setting a body condition.

When the body condition is set, a second guide screen 572 includes exercise guide information guiding an exercise. The exercise guide information may include a type of an exercise, a recommended exercise hour, and a description of an exercise type. The user may select a desired exercise from among various types of exercise data, or the number for times of doing exercise, a time duration, and the like.

The control unit 180 may control the display unit 151 to output a third guide screen 573 including preview information regarding a selected exercise. Upon viewing the preview information, the user may change a type of an exercise or may adjust an exercise hour for doing exercise. The preview information may include video related to an exercise.

The display unit 151 outputs a fourth guide screen 574 for setting an exercise schedule. The fourth guide screen 574 may include a graphic image for setting an alarm indicating doing exercise. Although not specifically shown, in the fourth guide screen 574, performing a body fat measurement after the lapse of a preset period of time, before or after doing exercise may be set.

Although not specifically shown, the control unit 180 may control the display unit 151 to output alarm information on the basis of a set exercise schedule and output a graphic image reflecting an amount of performed exercise. The user may recognize whether the set amount of exercise has been performed. Also, the control unit 180 may output additional information according to whether a preset amount of exercise is performed. For example, the additional information may be an increase/decrease in premium (insurance), an increase/decrease in a hospital bill, and the like. For example, when the user does not perform all of the preset amounts of exercise, the control unit may provide additional information indicating that the premium will be increased. The additional information may be virtual information and may correspond to an alarm message instructing the user to do a preset amount of exercise.

According to the present embodiments, since the mobile terminal provides guide data guiding exercise and eating habits by using the measured body fat result information and a body condition desired by the user, the user may manage his or her health according to the body fat measurement result.

Figure 17:
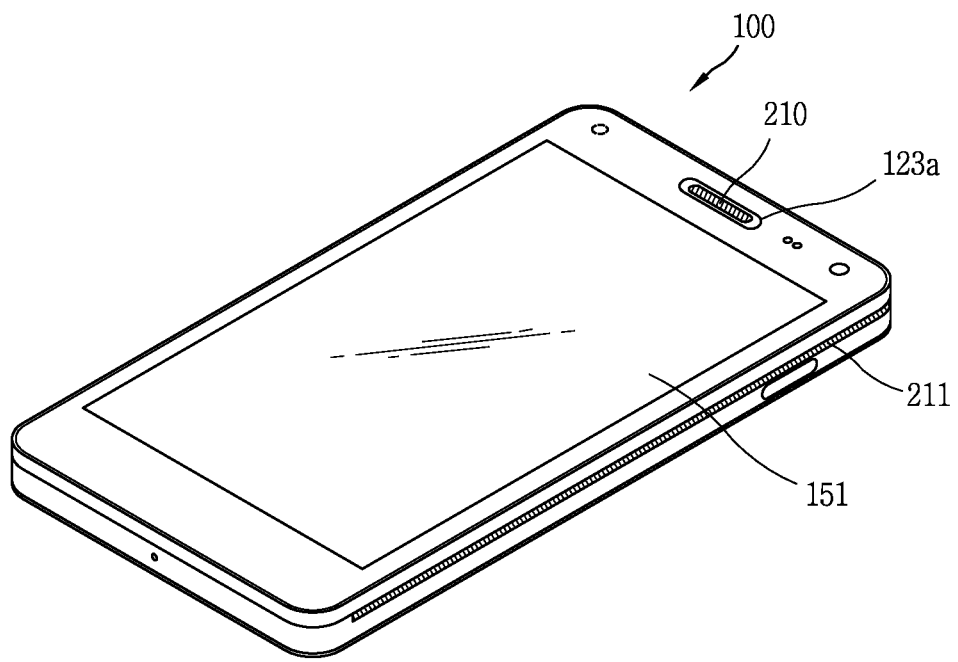
FIG. 17 is a view illustrating a mobile terminal including first and second electrode units according to another embodiment of the present disclosure viewed in one direction.

FIG. 17 is a view illustrating a mobile terminal including first and second electrode units according to another embodiment of the present disclosure viewed in one direction.

Referring to FIG. 17, components other than the first and second electrode units disposed on an outer surface of the terminal body are substantially the same as those of the mobile terminal 100. thus, the same reference numerals will be used for the same components, and a repeated description thereof will be omitted.

Referring to FIG. 17, the mobile terminal 100 includes first and second electrode units 210 and 211 which are distinguished from each other. When a part of the body of the user comes into contact with the first and second electrode units 210 and 211, a closed loop is formed and a current flows. The control unit 180 may form impedance information according to a voltage between the first and second electrode units 210 and 211. The first and second electrode units 210 and 211 may be formed of a metal.

For example, the first electrode unit 210 may be formed to be adjacent to the first audio output unit 152a. Accordingly, when the user puts the first audio output unit 152 to his or her ear (for example, when a call function is performed), the first electrode unit 210 may come into contact with the user's body.

The second electrode unit 211 may be formed on a side surface of the main body of the mobile terminal 100. The second electrode unit 211 may be formed to be exposed on the side surface. The first and second electrode units 210 and 211 may be disposed to be spaced apart from one another. The second electrode unit 211 may be formed in a region with which a part of the user's body mostly comes into contact, and the first electrode unit 210 may be formed in a region of the terminal body which comes into contact with the user's body in a specific situation or while a specific function is performed.

The mobile terminal according to the present embodiment does not need to interwork with an electrode unit included in an external device. Impedance information may be formed when the user holds the mobile terminal 100 in his or her hand and the user's body is in contact with only the second electrode unit 211 and when a call function is performed and the user's body is in contact with both the first and second electrode units 210 and 211.

When the mobile terminal 100 interworks with an external device 200 including another electrode unit. The control unit 180 may perform control such that a current is not output from the external device 300 on the basis of a user setting. Alternatively, impedance information of each body part may be more minutely divided and formed by using the first and second electrode units included in the mobile terminal and the electrode unit of the external device 300.

FIGS. 18A through 19C are views illustrating a mobile terminal including two electrode units.

Figure 18A:
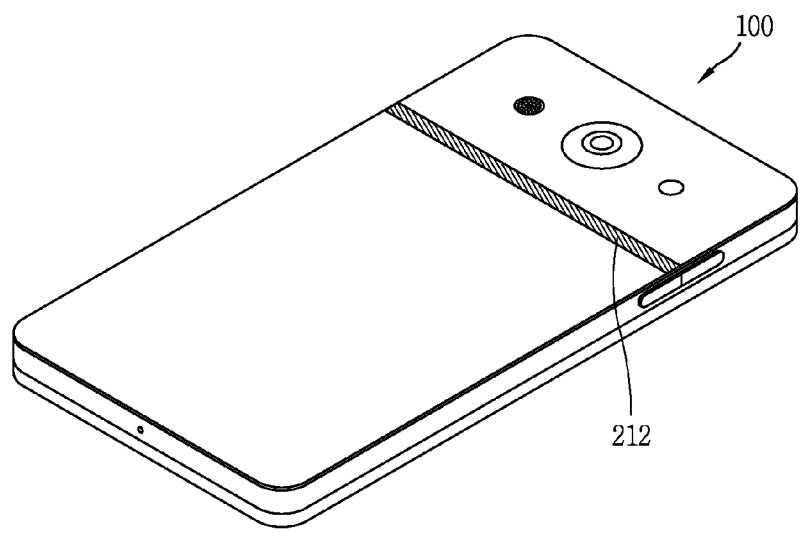
FIGS. 18A and 18B are views illustrating a mobile terminal including two electrode units.
Figure 18B:
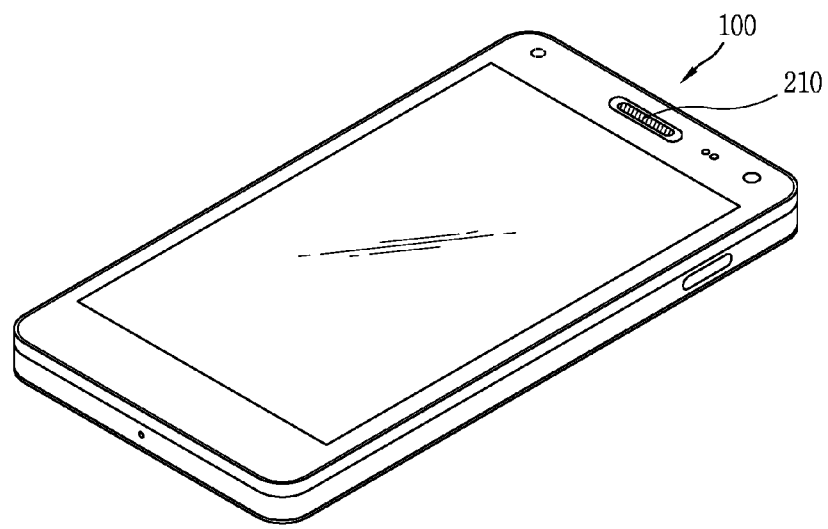
Figure 19A:
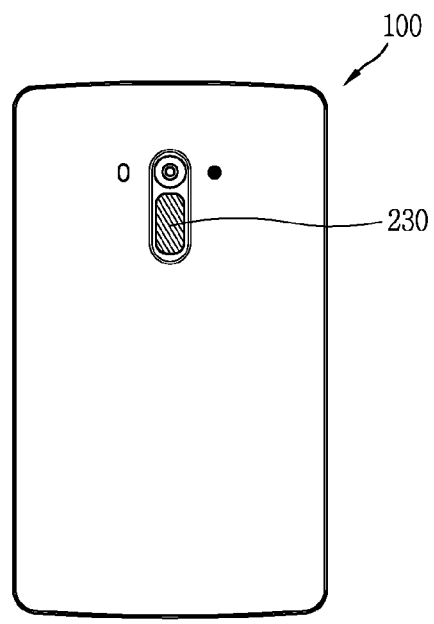
FIGS. 19A through 19C are views illustrating a mobile terminal including two electrode units.
Figure 19B:
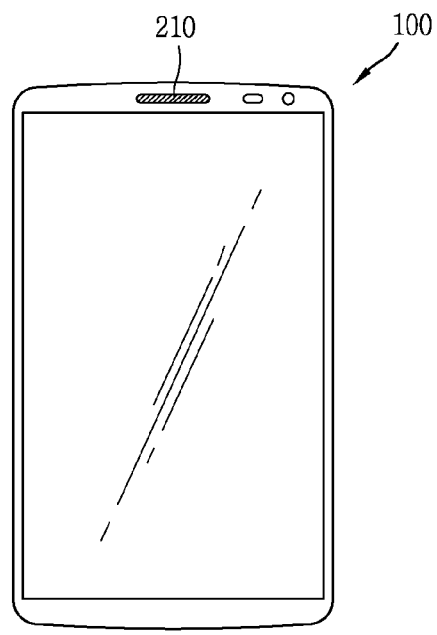
Figure 19C:
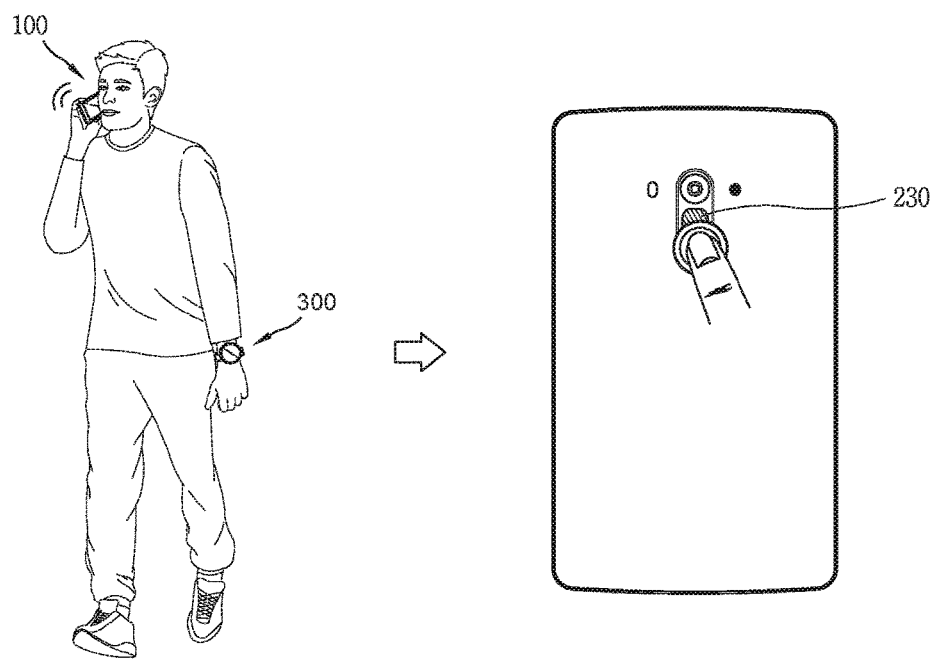

FIGS. 18A and 18B are views illustrating a mobile terminal according to an embodiment of the present disclosure viewed in different directions. The mobile terminal according to the present embodiment includes first and second electrode units 210 and 212 formed in different regions. The second electrode unit 210 is formed to be adjacent to the first audio output unit 152a, and is substantially the same as the second electrode unit 210 of FIG. 12.

The first electrode unit 210 may be formed on a rear surface of the main body of the mobile terminal 100. The first electrode 210 may be formed of a metal extending in one direction. The first electrode unit 210 may be formed in a region which can be almost in contact with the user's hand when the user uses the mobile terminal.

Referring to FIGS. 19A through 19C, FIGS. 2B, and 4B, the mobile terminal according to the present embodiment may include a first electrode unit 210 disposed to be adjacent to the first audio output unit 152a and a second electrode unit 230 formed to be adjacent to the rear key 123c.

When a call function is executed and the user's ear is in contact with the first electrode unit 210, the control unit 180 may output guide information instructing the user to put his or her finger to the second electrode unit 230.

The present invention described above may be implemented as a computer-readable code in a medium in which a program is recorded. The computer-readable medium includes any type of recording device in which data that can be read by a computer system is stored. The computer-readable medium may be, for example, a hard disk drive (HDD), a solid state disk (SSD), a silicon disk drive (SDD), a ROM, a RAM, a CD-ROM, a magnetic tape, a floppy disk, an optical data storage device, and the like. The computer-readable medium also includes implementations in the form of carrier waves (e.g., transmission via the Internet). Also, the computer may include the controller 180 of the terminal. Thus, the foregoing detailed description should not be interpreted limitedly in every aspect and should be considered to be illustrative. The scope of the present invention should be determined by reasonable interpretations of the attached claims and every modification within the equivalent range are included in the scope of the present invention.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

What is claimed is:

1. A mobile terminal, comprising:
a terminal body;
a wireless communication unit configured to perform wireless communication with an external device that includes a first electrode unit positionable to permit contact with a part of a user's body;
a second electrode unit arranged in the terminal body to permit contact with another part of the user's body to form a closed loop with the first electrode unit; and
a controller configured to:
obtain a body fat measurement using a voltage formed by a current flowing between the first electrode unit and the second electrode unit when the first electrode is in contact with the part of the user's body and the second electrode unit is in contact with the another part of the user's body, and
control the second electrode unit to output the current to form an impedance when a specific function is executed, wherein the specific function is execution of a specific application for outputting a result of the body fat measurement.

2. The mobile terminal of claim 1, further comprising:
an audio output unit, wherein the second electrode unit is located adjacent to the audio output unit.

3. The mobile terminal of claim 2, wherein the controller is further capable of:
identifying impedance using the voltage between first electrode unit and the second electrode unit when a call function is performed with an external terminal and when the second electrode is sensed as being in contact with the another part of the user's body.

4. The mobile terminal of claim 3, wherein the controller is further capable of:
causing the wireless communication unit to transmit the result of the body fat measurement to the external terminal when the call function is performed and when the external terminal is a preset terminal.

5. The mobile terminal of claim 1, wherein the specific function is an alarm function outputting alarm information at a preset time.

6. The mobile terminal of claim 5, further comprising:
a camera; and
wherein the controller is further capable of:
controlling the second electrode unit to output the current to form the impedance when a preset user's face is recognized in an image captured by the camera.

7. The mobile terminal of claim 1, wherein the controller is further capable of:
outputting an audio or visual notification indicating measurement of the voltage between the first electrode unit and the second electrode unit while the impedance is being formed.

8. The mobile terminal of claim 1, further comprising:
a display; and
wherein the controller is further capable of:
controlling the display to display a notification image in accordance with the obtaining of the body fat measurement; and
executing the specific application in response to an input received with regard to the displayed notification image.

9. The mobile terminal of claim 8, wherein the controller is further capable of:
obtaining the body fat measurement regarding a part of the user's body between which the first electrode and the second electrode are placed in contact with the user's body.

10. The mobile terminal of claim 9, further comprising:
a memory; and
wherein the controller is further capable of:
storing in the memory information regarding the part of the user's body at which the first electrode unit is positioned.

11. The mobile terminal of claim 10, wherein the controller is further capable of:
controlling the display to display a result of a body fat measurement of a plurality of parts of the user's body; and
controlling the display to display a guide screen guiding a contact positioning of the second electrode unit to measure impedance of a part of the user's body selected from among the plurality of pieces of result information.

12. The mobile terminal of claim 1, wherein the controller is further capable of:
obtaining guide information according to a result of the body fat measurement and a preset target fat mass, wherein the guide information includes exercise information and food intake information.

13. The mobile terminal of claim 12, wherein the controller is further capable of:
outputting guide information guiding re-measurement when a fat mass included in the body fat measurement exceeds a preset reference value.

14. The mobile terminal of claim 1, further comprising:
an input key located in the terminal body to receive user input, wherein the second electrode is adjacent to the input key.

15. The mobile terminal of claim 1, wherein the terminal body includes a front side, a rear side, and edge side adjacent to both the front side and the rear side, wherein the terminal further comprises:
a display located on the front side, wherein the second electrode unit is located on the edge side.

16. The mobile terminal of claim 1, further comprising:
a third electrode unit formed in a region of the terminal body that is different from the second electrode unit;
wherein the controller is further capable of:
performing a further body fat measurement using a voltage formed by a current flowing between the second electrode unit and the third electrode unit.

17. The mobile terminal of claim 16, wherein the controller is further capable of:
outputting guide information when user contact with one of the second electrode unit or the third electrode unit is detected, wherein the guide information guides to a portion of the user's body to place another one of the second electrode unit or the third electrode unit.

18. A measuring method for a mobile terminal, the method comprising:
performing wireless communication with an external device that includes a first electrode unit positionable to permit contact with a part of a user's body;
outputting a current when a second electrode unit arranged in a body of the terminal comes into contact with an other part of the user's body;
measuring a voltage between the first electrode unit and the second electrode unit;
obtaining a body fat measurement using a voltage formed by current flowing between the first electrode unit and the second electrode; and
controlling the second electrode unit to output the current to form an impedance when a specific function is executed, wherein the specific function is execution of a specific application for outputting a result of the body fat measurement.

19. The method of claim 18, further comprising:
storing in memory of the mobile terminal body information of the user;
identifying the impedance using the voltage between first electrode unit and the second electrode unit; and
obtaining the result of the body fat measurement using the body information and the impedance,
wherein the body information includes at least one of a height, a weight, a gender, or age.

* * * * *